United States Patent [19]
Eugster et al.

[11] Patent Number: 5,496,813
[45] Date of Patent: Mar. 5, 1996

[54] SPONTANEOUSLY DISPERSIBLE CONCENTRATES AND AQUEOUS MICROEMULSIONS WITH STERYL RETINATES HAVING ANTI-TUMOR ACTIVITY

[75] Inventors: Carl Eugster, Riehen; Conrad H. Eugster, Wallisellen; Walter Haldemann, Binningen, all of Switzerland; Giorgio Rivara, Turin, Italy

[73] Assignee: Marigen S.A., Riehen, Switzerland

[21] Appl. No.: 3,997

[22] Filed: Aug. 13, 1992

[63] Continuation-in-part of PCT/CH91/00221, Oct. 25, 1991, abandoned.

[30] Foreign Application Priority Data

Jan. 28, 1991 [CH] Switzerland ............... CH06257/91

[51] Int. Cl.$^6$ .................... A61K 31/58; A61K 31/575; A61K 31/57; A61K 31/565
[52] U.S. Cl. ............... 514/172; 514/171; 514/182; 540/114; 540/117; 552/544; 552/547; 552/552; 552/555; 552/599; 552/603; 552/606; 552/609; 552/611; 552/625; 552/627
[58] Field of Search ................... 552/555, 552, 552/544, 547, 625, 627, 603, 606, 609, 611, 599; 514/171, 182, 172; 540/114, 117

[56] References Cited

U.S. PATENT DOCUMENTS

| 4,190,594 | 2/1980 | Gander et al. | |
| 5,270,041 | 12/1993 | Eugster et al. | 552/540 |

FOREIGN PATENT DOCUMENTS

| 0375349 | 6/1990 | European Pat. Off. | |
| 678276 | 8/1991 | Switzerland | A61K 31/575 |
| 91/05754 | 5/1991 | WIPO | |

OTHER PUBLICATIONS

Mahendra K. Jain et al., "Phosphatidylcholesterol Bilayers A Model for Phospholipid–Cholesterol Interaction", Biochimica et Biophysica Acta, 600 (1980), Elsevier/North-–Holland Biomedical Press, pp. 678–688.

Toshio Muramatsu et al., "Synthesis of Phospholipids. III. Synthesis of 1,2–Dipalmitoyl–rac–Glyceryl– . . . ", Chemistry and Physics of Lipids, 20 (1977), Elsevier/North–Holland Scientific Publ. Ltd., pp. 131–139.

I. Hara et al., "Immunochemical Properties of Phosphatidyl Cholesterol and its Homologue", Chemistry and Physics of Lipids, 23 (1979), Elsevier/North–Holland Scientific Publ., Ltd., pp. 2–12.

J. H. Noggle et al., "Bilayers of Phosphatidyldiacylglycerol and Phosphatidylcholesterol Give $^{31}$P–NMR . . . ", Biochimica et Biophysica Acta, 691 (1982), Elsevier Biomedical Press, pp. 240–248.

Fausto Ramirez et al., "Covalent Models for Phospholipis-–sterol Interactions. Synthesis of Phosphatidyl . . . ", Phosphorus and Sulfur, 1983, vol. 17, Gordon and Breech Science Publ. Inc., pp. 67–71.

Fausto Ramirez et al., "Synthesis of Phospholiposteriods. Phosphatidylcholesterol", Communications, Oct. 1977, pp. 673–675, [A. K. Singh, Chemical Abstracts, 97:110220g (1982) p. 634].

Vazquez–Alcantara et al., Chemical Abstracts, 112:151977f (1990) p. 93.

Vazquez–Alcantara et al., Chemical Abstracts, 104:62329p (1986) p. 94.

Gomez et al., Chemical Abstracts, 100:99762t (1984) p. 347.
Jain et al., "Lateral Interaction of Cholesterol in Diacylphosphatidylcholesterol Bilayers", Biochimica et Biophysica Acta, 775 (1984), Elsevier Science Publ. B.V., pp. 426–434.

*Primary Examiner*—Kimberly J. Kestler
*Attorney, Agent, or Firm*—Foley & Lardner

[57] ABSTRACT

There are described spontaneously dispersible agents containing sterolester and/or sterolphosphor compounds having a pronounced antitumour activity. Novel sterolesters and sterolphosphor compounds, their use for treating tumors, and processes for their preparation are disclosed.

9 Claims, 7 Drawing Sheets

| CHEMICAL SHIFT IN PPM VS. TMS*) | MULTIPLICITY **) | NUMBER OF PROTONS | ASSIGNMENTS |
|---|---|---|---|
| 7.26 | s | SOLVENT | $CHCl_3$ |
| 7.0 | d, d | 1 | H-5' |
| 6.27 | m | 2 | H-4' + H-8' |
| 6.15 | d | 1 | H-9' |
| 6.10 | d | 1 | H-6' |
|  |  |  |  |
| 5.75 | s | 1 | H-2' |
| 5.57 | m | 1 | H-6 |
| 5.38 | m | 1 | H-7 |
| 5.25 ... 5.13 | m | 2 | H-22 + H-23 |
| 4.75 | m | 1 | H-3α |
|  |  |  |  |
| 2.35 | s (m) | 3 | $-CH_3$ (C-3') |
| 2.0 | s (m) | 3 | $-CH_3$ (C-7') |
| 1.70 | s (m) | 3 | $-CH_3$ (C-15') |
| 1.25 + 1.0 | s + s | 6 | $-C{<}^{CH_3}_{CH_3}$ (C-11') |
| 1.03 + 0.91 | d + d | 6 | sec. $CH_3$ (C-20 + C-24) |
| 0.96 | s | 3 | $-CH_3$ -19 |
| 0.83 + 0.82 | d + d | 6 | $-CH{<}^{CH_3\ 26}_{CH_3\ 27}$ |
| 0.63 | s | 3 | $-CH_3$ -18 |
| 2.5 ... 0.7 | m | REMAINING PROTONS |  |

SPONTANEOUSLY DISPERSIBLE CONCENTRATES AND AQUEOUS MICROEMULSIONS WITH STERYL RETINATES HAVING ANTI-TUMOR ACTIVITY

This application is a continuation-in-part of PCT/CH91/00221, Oct. 25, 1991 now abandoned.

INTRODUCTION

The present invention relates to spontaneously dispersible agents containing sterolesters and sterolphosphatides; to new sterolesters and sterolphos-phatides; to processes for their preparation, and to the use of the inventive spontaneously dispersible agents for the treatment of tumours.

In the CH-Patent No. 678276-0 are described sterols, their glucosides and their fatty acid esters, extracted from the seeds of sunflower (Helianthus annuus L.) and of certain pumpkin species (Cucurbita pepo L. and Cucurbita maxima, Duch.), as well as the spontaneously dispersible agents prepared with these compounds, and their use for the treatment of tumours.

Surprisingly, it has been found that the newly synthetised sterolesters and sterolphosphatides also have an outstanding antitumour activity, particularly if these compounds are being incorporated into spontaneously dispersible concentrates.

DESCRIPTION OF THE INVENTION

The sterolesters and sterolphosphorous compounds to be used according to the present invention correspond to the general formulae (I) to (XV):

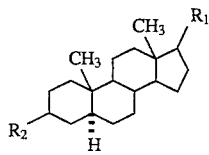 (I)

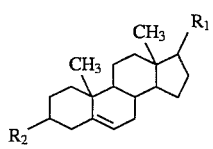 (II)

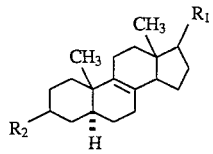 (III)

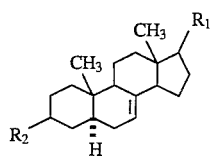 (IV)

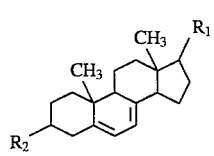 (V)

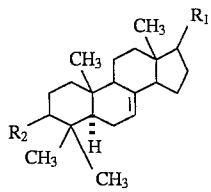 (VI)

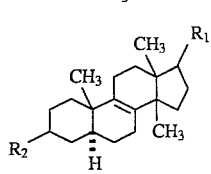 (VII)

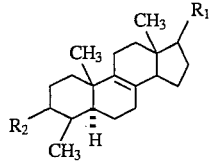 (VIII)

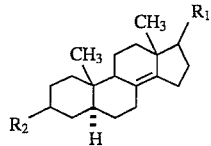 (IX)

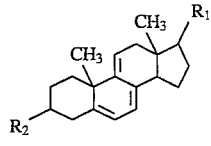 (X)

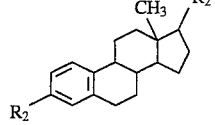 (XI)

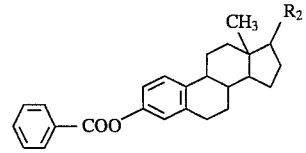 (XII)

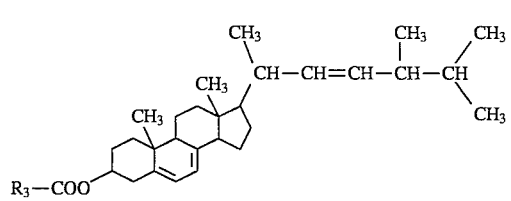 (XIII)

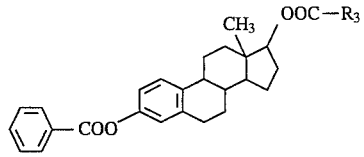 (XIV)

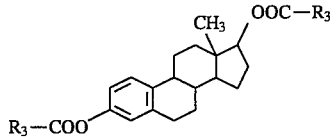 (XV)

whereby in the formulae (I) to (X) $R_1$ denotes a $C_1$- to $C_{10}$-alkyl or a $C_2$- to $C_{10}$-alkenyl group, and in the formulae (I) bis (XII) $R_2$ stands for a group of the formulae (XVI) and (XVII) respectively:

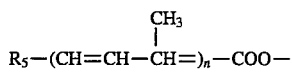 (XVI)

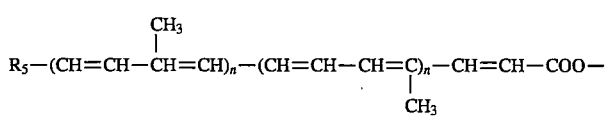 (XVII)

in which n means the numbers 1, 2, 3, 4 or 5 and $R_5$ stands for one of the radicals of the following formulae:

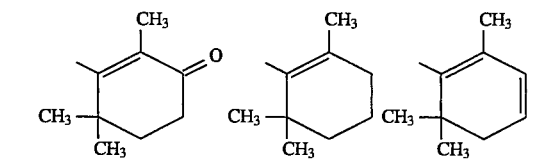

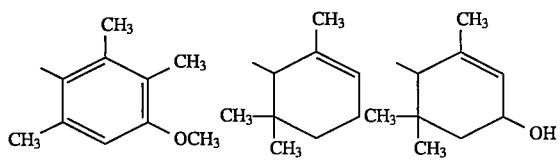

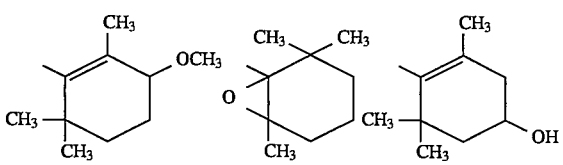

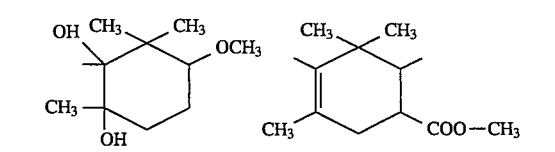

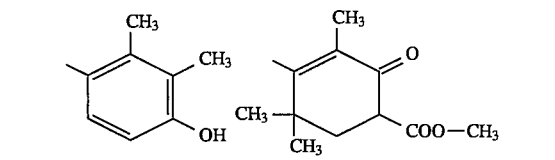

or

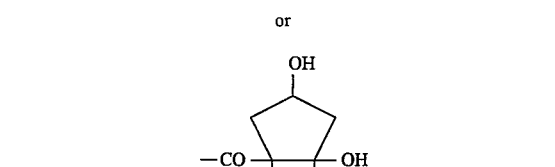

or represents the group of the formula (XVIII):

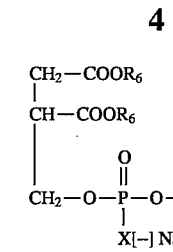 (XVIII)

in which $R_6$ denotes a $C_1$ to $C_{32}$-alkyl or a $C_2$ to $C_{32}$-alkenyl group and X represents an oxygen, sulfur or selenium atom, and in the formulae (XIII) to (XV) $R_3$ denotes a $C_4$ to $C_{32}$-alkyl and a $C_4$ to $C_{32}$-alkenyl/alkapolyene group (i.e. the corresponding alkadiene, alkatriene, alkatetraene, alkapentaene, alkahexaene or alkaheptaene groups).

The side chains of the radicals $R_1$, $R_3$ and $R_6$ may be straight chained or branched. In the case of $R_1$, the alkyl groups and the alkenyl groups preferably have 8 to 10 carbon atoms.

Examples of such groups are, inter alia:

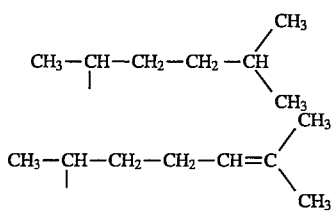 1

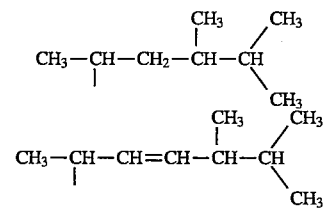 2

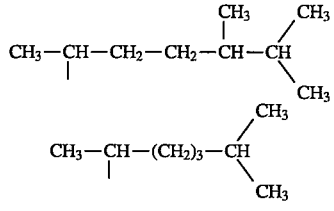 3

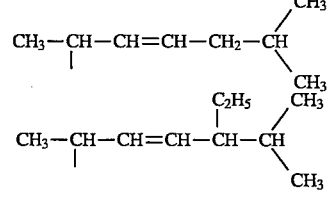 4

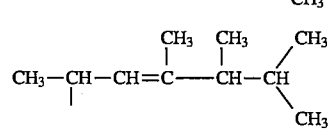 5

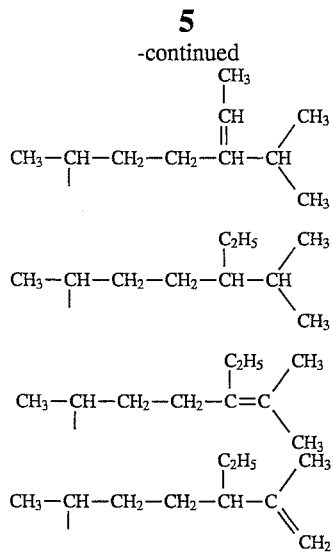

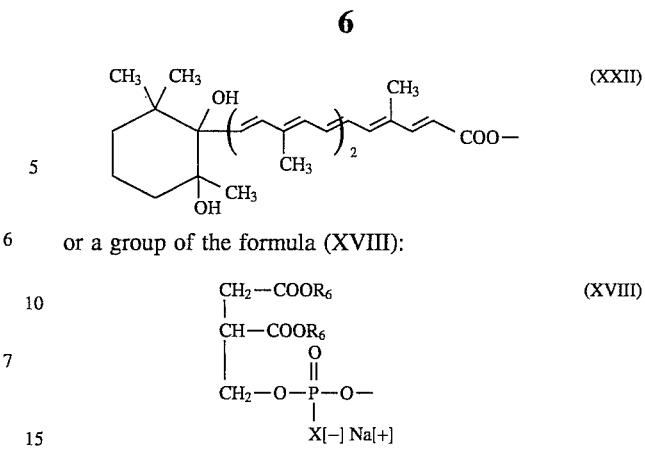

or a group of the formula (XVIII):

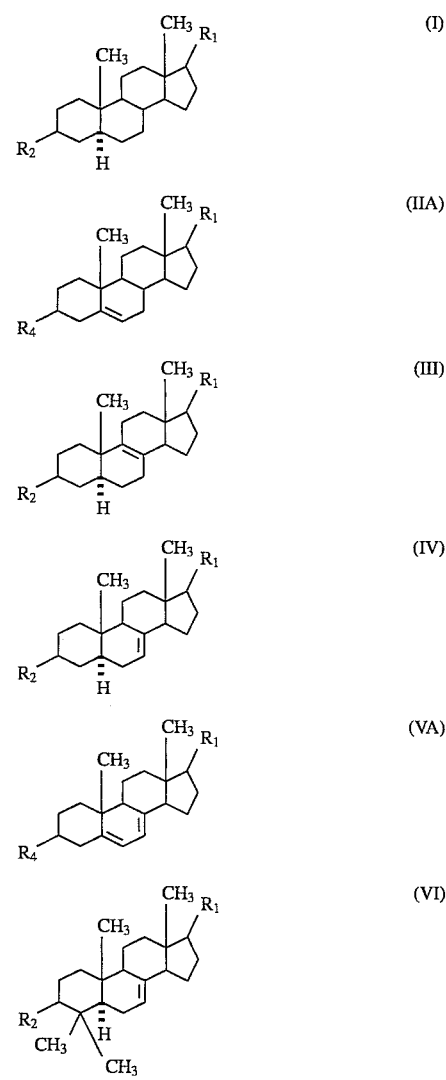

In the case of $R_3$ and $R_6$, the alkyl and alkenyl/alkapolyene groups (with 1 to 7 double bonds) chiefly have 4 to 22 carbon atoms. In the case of $R_3$ and $R_6$, particularly preferred alkyl and alkenyl/alkapolyene groups are those having 10 to 20 carbon atoms. The most important groups of the formulae (XVI) and (XVII) are represented by the formulae (XX) and (XXI):

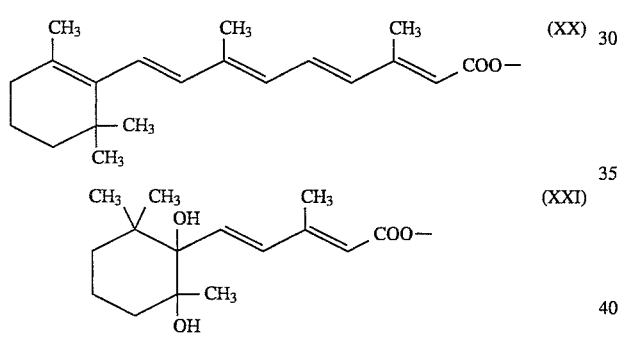

The group of the formula (XX) may have different stereoisomeric forms, such as e.g. the all trans, the 9-cis or the 13-cis form.

The most important group of the formula (XVIII) is characterized by the formula (XXII):

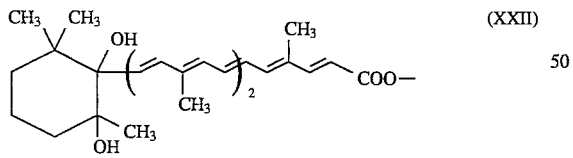

Of particular relevance are compounds of the formulae (I) to (XV), in which for the formulae (I) to (X) the radical $R_1$ signifies a $C_1$ to $C_{10}$-alkyl or a $C_2$ to $C_{10}$-alkenyl group and the radical $R_2$ in the formulae (I) to (XII) stands for a compound of the formula (XX):

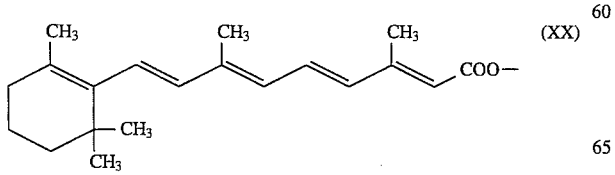

or a compound of the formula (XXII):

in which $R_6$ denotes a $C_1$ to $C_{32}$-alkyl or a $C_2$ to $C_{32}$-alkenyl group and X represents an oxygen or sulfur or selenium atom, and in the formulae (XIII) to (XV) $R_3$ denotes a $C_4$ to $C_{32}$-alkyl and a $C_4$ to $C_{32}$-alkenyl/alkapolyene group respectively.

The following sterolesters and sterolphosphatides to be used according to the invention are novel and likewise form part of the present invention. These new sterolesters and sterolphosphatides correspond to the general formulae (I), (IIA), (III), (IV), (VA), (VI) to (IX), (XA) and (XI) to (XIII):

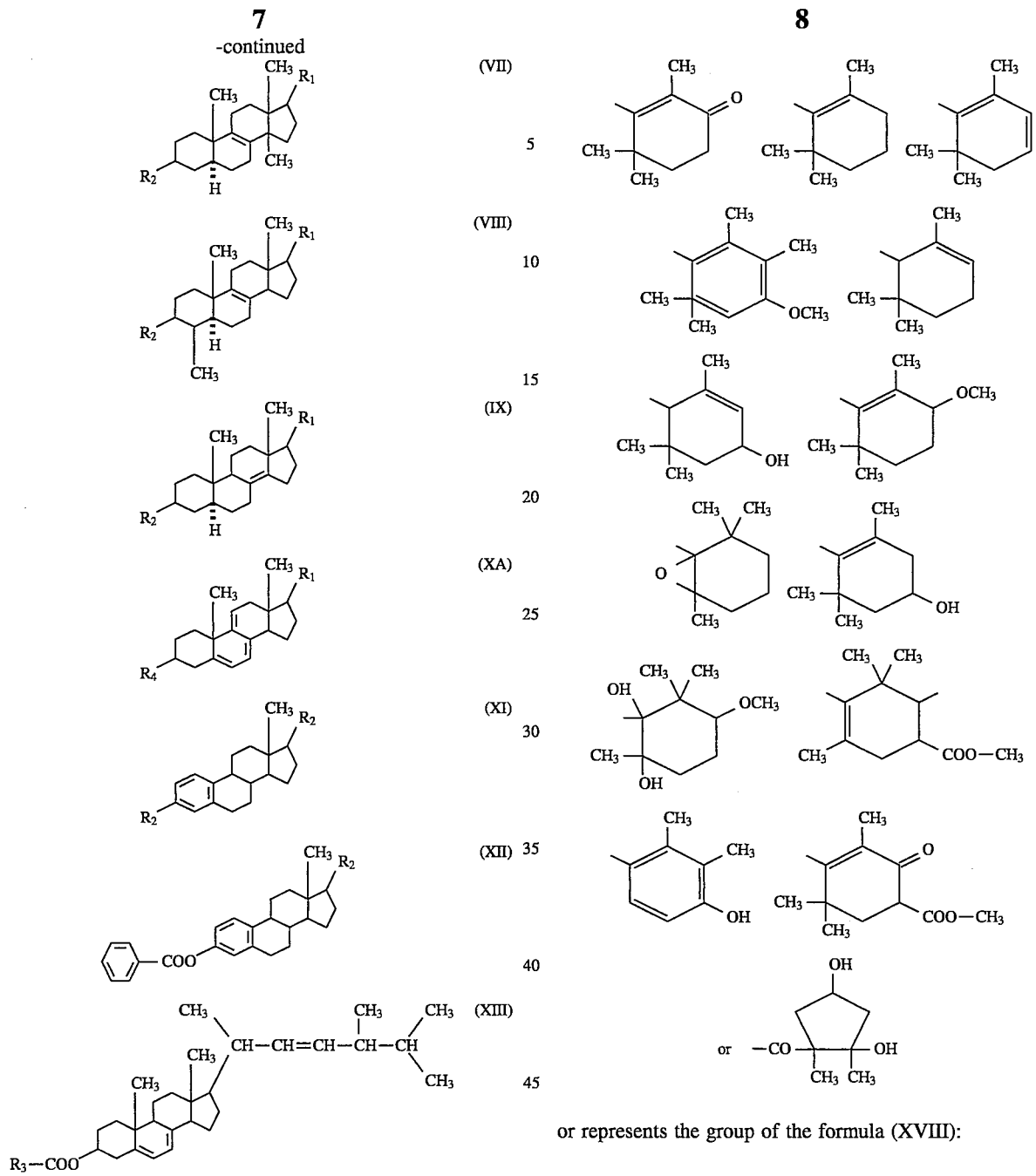
whereby in the formulae (I) to (XA) $R_1$ denotes a $C_1$ to $C_{10}$-alkyl or a $C_2$ to $C_{10}$-alkenyl group, and in the formulae (I) to (XII) $R_2$ stands for a group of the formulae (XVI) and (XVII) respectively:
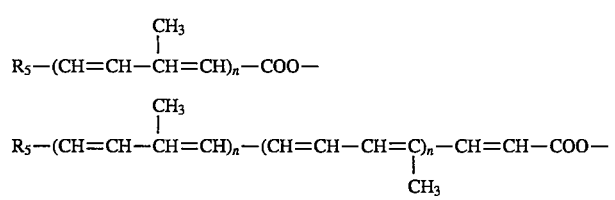
in which n means the numbers 1, 2, 3, 4 or 5 and $R_5$ stands for one of the radicals of the following formulae:

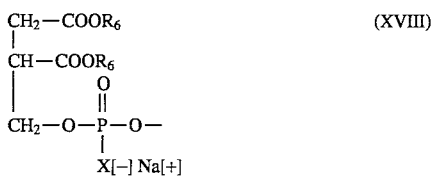

(XVIII)

in which $R_6$ denotes a $C_1$ to $C_{32}$-alkyl or a $C_2$ to $C_{32}$-alkenyl group and X represents an oxygen, sulfur or selenium atom, and in the formula (XIII) $R_3$ designates a $C_4$ to $C_{32}$-alkyl or a $C_4$ to $C_{32}$- alkenyl/alkapolyene group (i.e. the corresponding alkadiene, alkatriene, alkatetraene, alkapentaene, alkahexaene or alkaheptaene groups) and in the formulae (IIA), (VA) and (XA) $R_4$ stands for a group of the formulae (XVI) and (XVII) respectively:

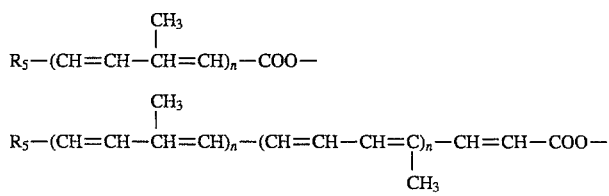

(XVI)

(XVII)

in which n means the numbers 1, 2, 3, 4 or 5, with the proviso, however, that $R_4$ in the formula (IIA) cannot designate the known compound cholest-5-en-3-all-trans-retinate.

Of particular relevance are the new sterolesters and sterolphosphatides of the general formulae: (I), (IIA), (III), (IVA), (V) to (IX) (XA) and (XI) to (XIII), in which for the formulae (I) up to (XA) the radical $R_1$ signifies a $C_1$ to $C_{10}$-alkyl or a $C_2$ to $C_{10}$-alkenyl group and the radical $R_2$ in the formulae (I), (III), (IV), (VI) to (IX), (XI) and (XII) stands for a compound of the formula (XX):.

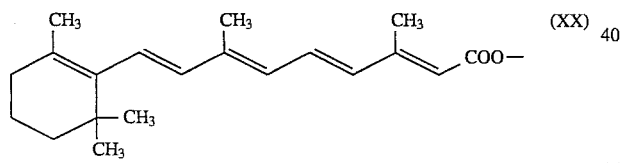

(XX)

or a compound of the formula (XXII):

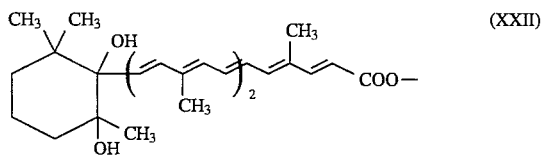

(XXII)

or represents the group of the formula (XVIII):

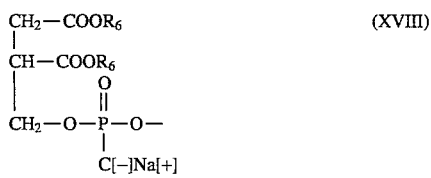

(XVIII)

in which $R_6$ denotes a $C_1$ to $C_{32}$-alkyl or a $C_2$ to $C_{32}$-alkenyl group and X represents an oxygen, sulfur or selenium atom, and in the formula (XIII) $R_3$ designates a $C_4$ to $C_{32}$-alkyl or a $C_4$ to $C_{32}$- alkenyl/alkapolyene group and in the formulae (IIA), (VA) and (XA):

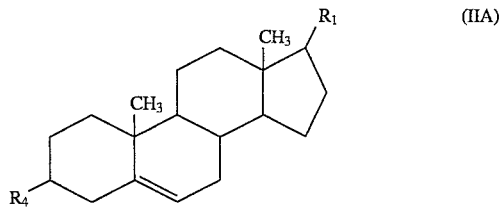

(IIA)

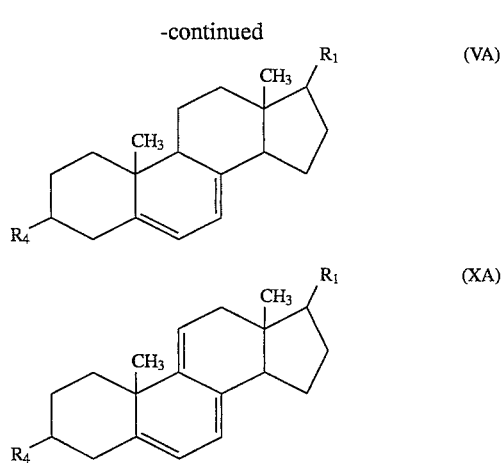

(VA)

(XA)

$R_4$ stands for a group of the formulae (XX) and (XXII) respectively:

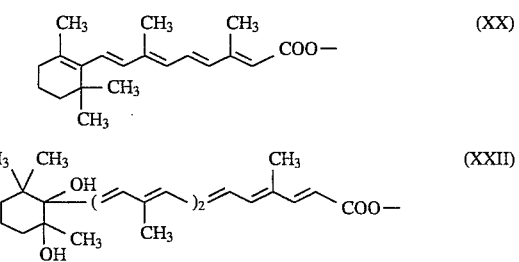

(XX)

(XXII)

with the proviso, however, that $R_4$ in the formula (IIA) cannot represent the known compound cholest-5-en-3-all-trans-retinate.

Examples of the inventive new sterolesters and sterol-phosphorous compounds of the formulae (I) to (VI) are, e.g.:
Ergosta-5,7,22-trien-3-ol-all-trans-retinate
Ergosta-5,7,22-trien-3-ol-13-cis-retinate
Cholest-5-en-13-cis-retinate
Stigmast-5-en-3-ol-all-trans-retinate
(β-Sitosterol-all trans-retinate)
Stigmast-5-en-3-ol-13-cis-retinate
(β-Sitosterol-13-cis-retinate)
Stigmast-5-en-3-ol-azafrinate Stigmasta-5,22-dien-3-ol-all trans-retinate
(Stigmasterol-all trans-retinate)
Stigmasta-5,22-dien-3-ol-13-cis-retinate
(Stigmasterol-13-cis-retinate)
Stigmasta-5,22-dien-3-ol-arachidonate
Stigmasta-5,22,dien-3-ol-azafrinate
Stigmasta-5,22-dien-3-ol-1,2-dipalmitoyl-glycero-phosphatide
Stigmasta-5,22-dien-3-ol-1,2-dipalmitoyl-glycero-thiophosphatide
Ergosta-5,7,22-trien-3-ol-1,2-dipalmitoyl-glycero-phosphatide
Ergosta-5,7,22-trien-3-ol-crotonate
Ergosta-5,7,22-trien-3-ol-caproylate
Ergosta-5,7,22-trien-3-ol-10-undecenoate
Ergosta-5,7,22-trien-3-ol-trans-2-dodecenoate
Ergosta-5,7,22-trien-3-ol-oleate
Ergosta-5,7,22-trien-3-ol-linoleate
Ergosta-5,7,22-trien-3-ol-linolenate
Ergosta-5,7,22-trien-3-ol-arachidonate
Ergosta-5,7,22-trien-3-ol-azafrinate
β-Estradiol-3,17-di-all trans-retinate
β-Estradiol-3-benzoate-17-all trans-retinate The new sterolesters and sterolphosphorous compounds of the formulae (I) (IIA), (III). (IV), (VA), (VI) to (IX) (XA) and (XI) to (XIII) may generally be prepared in semisynthetic procedure by the following processes, which are known per se:

a) Reaction of a compound of the formula (XXIII) or (XXIV):

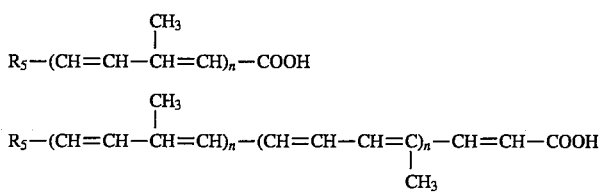

in which n means the number 1, 2, 3, 4 or 5 and $R_5$ denotes of the radicals of the following formulae:

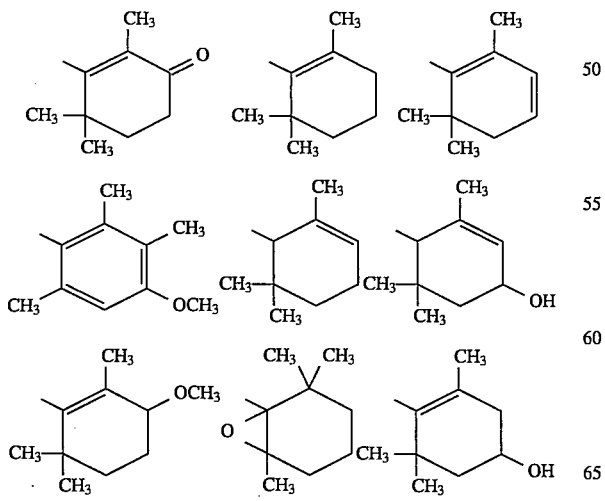

with N,N'-carbonyl-diimidazole at 25° to 70° C. with the addition of a catalytic amount of an alcoholate in tetrahydrofurane, benzene, chloroform or dimethylformamide or in a similar indifferent solvent, followed by alcoholysis of the imidazolides formed with a sterol of the formulae (XXV) to (XXXVII):

(XXIII)

(XXIV)

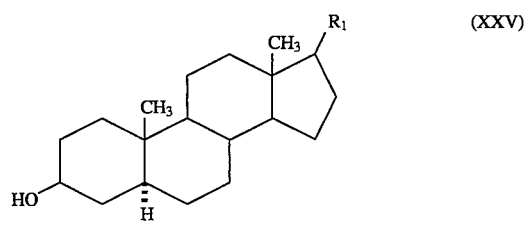
(XXV)

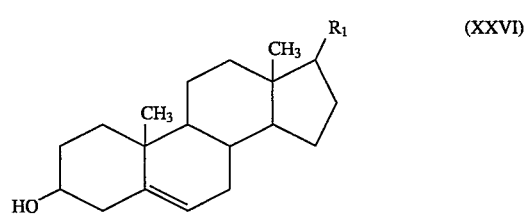
(XXVI)

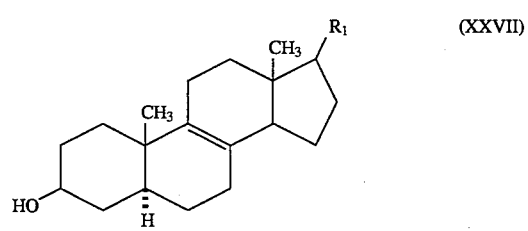
(XXVII)

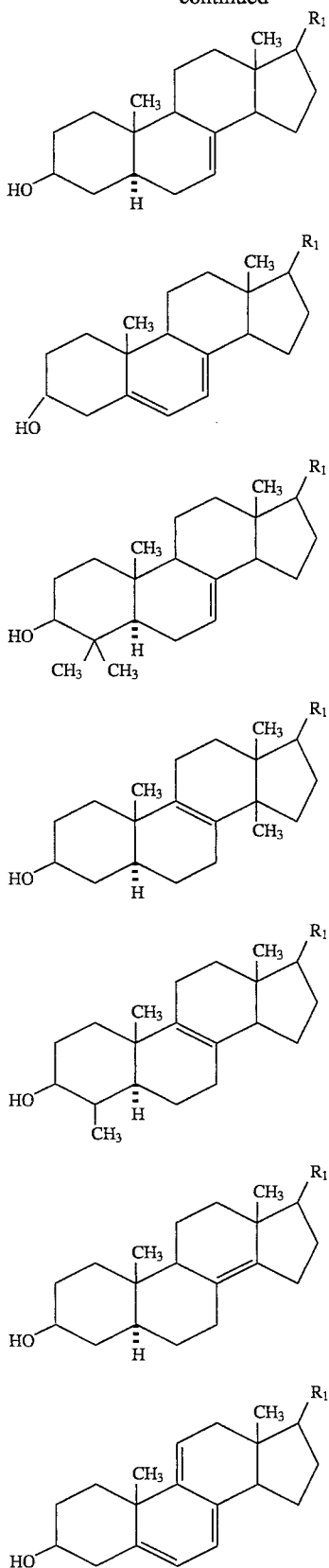
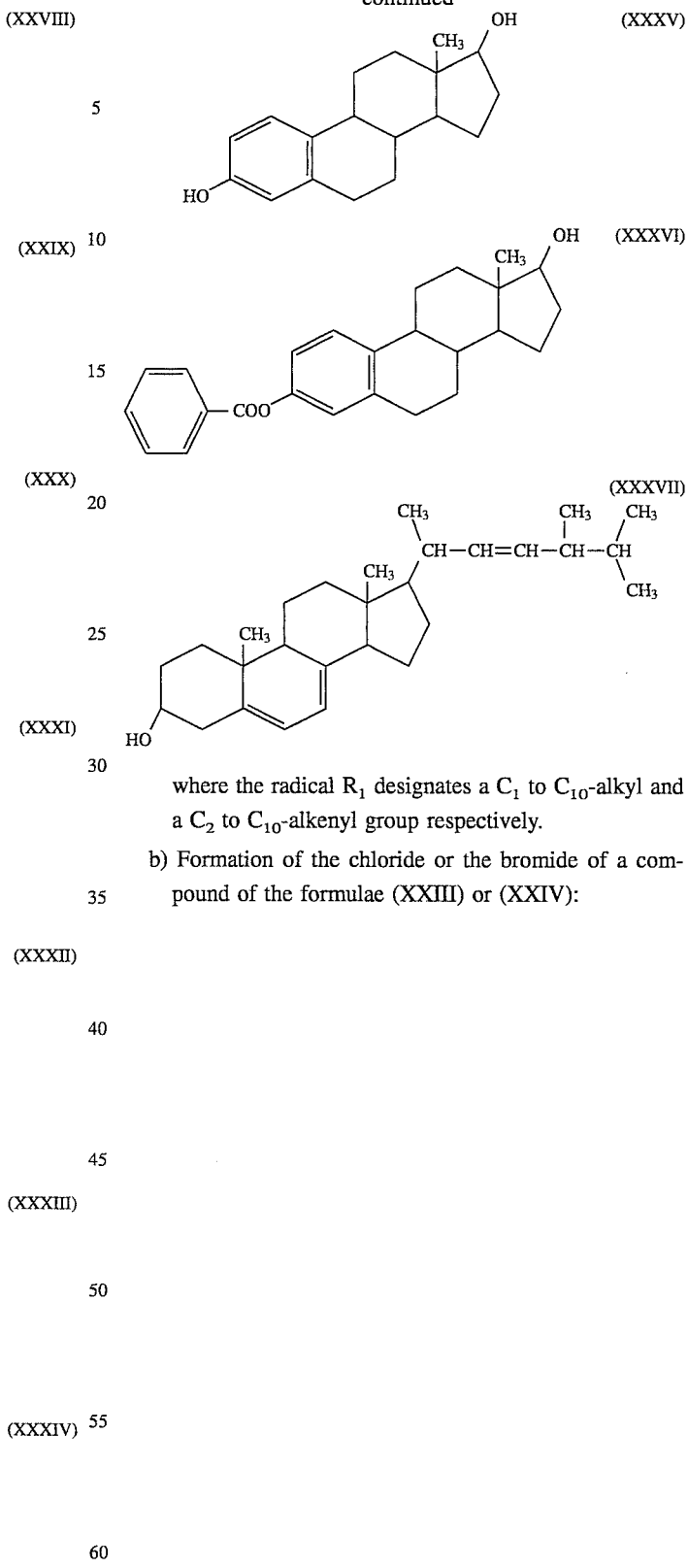
where the radical $R_1$ designates a $C_1$ to $C_{10}$-alkyl and a $C_2$ to $C_{10}$-alkenyl group respectively.
b) Formation of the chloride or the bromide of a compound of the formulae (XXIII) or (XXIV):

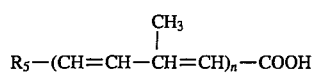

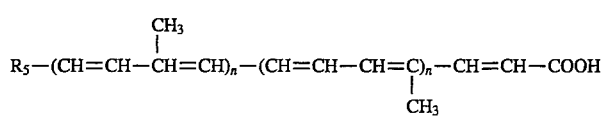

in which n means the number 1, 2, 3, 4 or 5 and $R_5$ denotes one of the radicals of the following formulae:

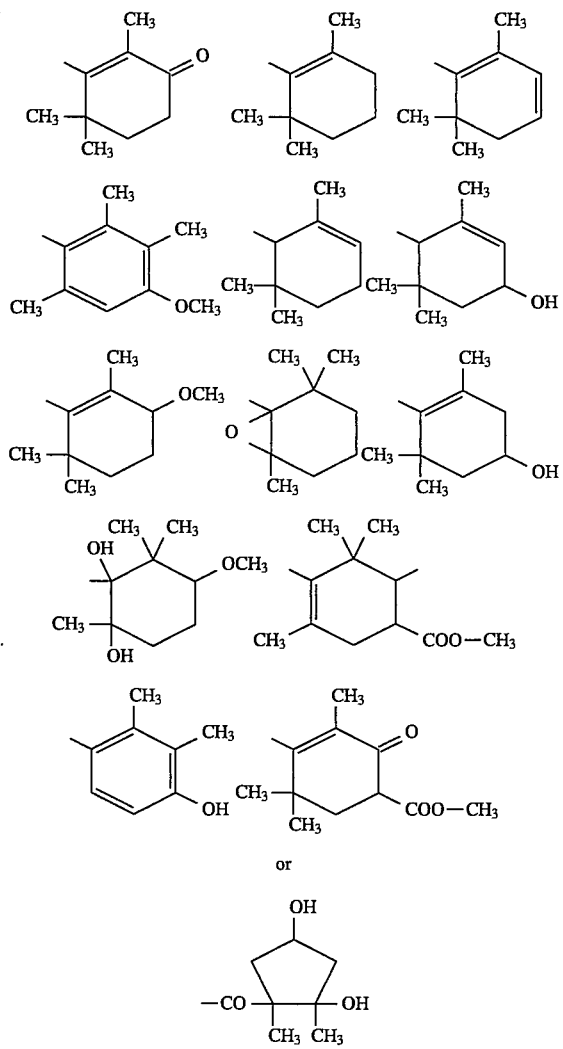

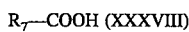

with a chlorination or bromination agent such as thionylchloride, oxalylchloride or oxalylbromide, followed by the reaction of the chloride or bromide formed with a sterol of the formulae (XXV) to (XXXVII) [via reaction a)] at a temperature of between 40° and 120° C. in an indifferent solvent such as toluene or xylene, and in the presence of a catalyst such as dimethylformamide or p-dimethylaminopyridine.

c) Chlorination or bromination of a compound of the formula (XXXVIII)

$R_7$—COOH (XXXVIII)

in which $R_7$ denotes a $C_4$ to $C_{32}$-alkyl group or a $C_4$ to $C_{32}$-alkenyl/alpolyene group, with a chlorination or bromination agent such as thionylchloride, oxalylchloride or oxalylbromide, followed by the reaction of the chloride or bromide formed with a sterol of the formulae (XXXV), or (XXXVI) or (XXXVII):

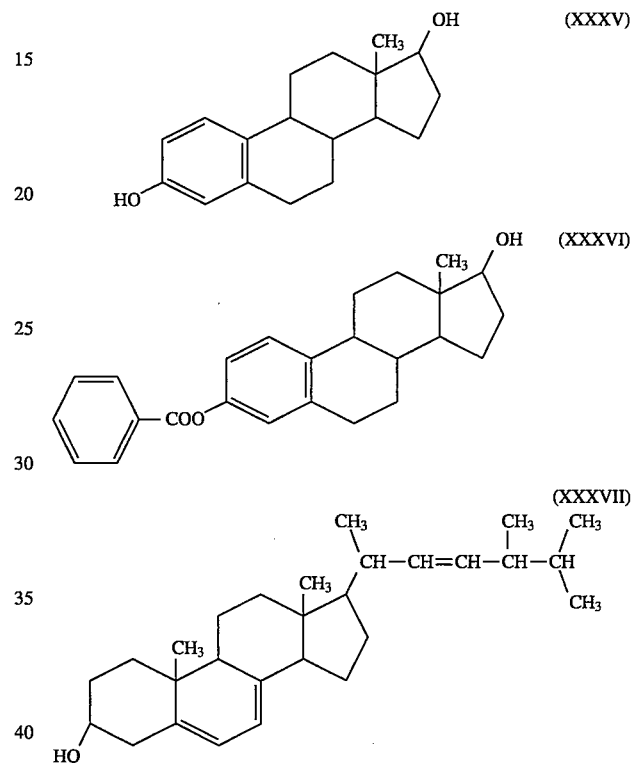

in an inert solvent such as e.g. carbon tetrachloride, chloroform. toluene or p-xylene, at a temperature of 40° to 120° C., and in the presence of a catalyst such as dimethylformamide oder p-dimethylaminopyridine.

d) Esterification of a compound of the formula (XXXVIII):

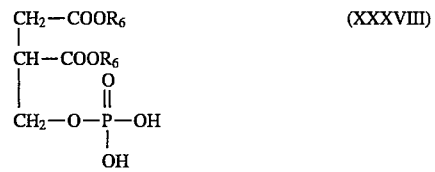

in which $R_6$ signifies a $C_1$ to $C_{32}$-alkyl group or a $C_2$ to $C_{32}$-alkenyl/alpolyene group, in an inert solvent such as pyridine, tetrahydrofurane or chloroform, at a temperature of 20° C. with pivaloylchloride, followed by the reaction of the product in the same solvent with a sterol of the formulae (XXV) and (XXVII) up to (XXXVII).

The new sterolesters and sterolphosphatides possess, surprisingly, excellent antitumour activity, most notably when these compounds have been incorporated into spontaneously dispersible concentrates.

For this reason, spontaneously dispersible concentrates made up with the new compounds of the formulae (I) to (XIII) are also a subject matter of the present invention. When treated with water, such concentrates render microemulsions having excellent phase stability as well as much improved membrane permeability and spreading properties.

These spontaneously dispersible concentrates prepared in accordance with the invention contain 0.001 to 25% by weight of individual sterolesters or sterolphosphorous compounds of the formulae (I) to (XV), or combinations of these compounds 0.001 to 40% by weight of a solvent or solvent mixture which is pharmaceutically acceptable and acts as a hydrotropic or coemulsifier 0.001 to 90% by weight of a pharmaceutically acceptable surfactant or surfactant mixture, and optionally up to 10% by weight of a vitamin or provitamin up to 10% by weight of a free fatty acid, and if appropriate, customary excipients and/or diluents.

The surfactants or surfactant mixtures to be employed according to the invention can be anionic, cationic, amphoteric or non-ionic. Ideally, they are non-ionic and have an HLB-value (i.e. a hydrophilic-lipophilic balance) of between 2 and 18; preferably, it is between 2 and 6 on the one hand and 10 and 15 on the other hand. HLB values describe the hydrophilic and lipophilic properties of an emulsifier. In this context see "Hydrophile-Lipophile Balance: History and recent Developments" by Paul Becher in Journal of Dispersion Science and Technology, 5 (1), 81–96 (1984).

Suitable anionic surfactants can be both so-called water-soluble soaps and water-soluble synthetic compounds. Suitable soaps are the alkali metal salts, alkaline earth metal salts or optionally substituted ammonium salts of higher fatty acids ($C_{12}$ to $C_{22}$), for example the natural Na or K salts of oleic or stearic acids, or of natural mixtures of fatty acids which can be obtained, inter alia, from coconut oil or tallow oil. Other surfactants which may be mentioned are fatty acid methyltaurine salts, and modified and non-modified phospholipids.

However, more frequently used surfactants are so-called synthetic surfactants, in particular fatty sulfonates, fatty sulfates, sulfonated benzimidazole derivatives or alkylarylsulfonates.

The fatty sulfonates and fatty sulfates are usually present in the form of alkali metal salts, alkaline earth metal salts or optionally substituted ammonium salts and generally have an alkyl radical containing 8 to 22 C atoms, alkyl also encompassing the alkyl moiety of acyl radicals. Examples are the Na or Ca salt of ligninsulfonic acid, of dodecylsulfuric ester and sulfonic acids of fatty alcohol/ethylene oxide adducts. The sulfonated benzimidazole derivatives preferably contain two sulfonyl groups and one fatty acid radical containing about 8 to 22 C atoms. Alkylarylsulfonates are, for example, the Na, Ca or triethanolamine salts of dodecylbenzenesulfonic acid, of dibutylnaph-thalenesulfonic acid or of a naphthalenesulfonic acid/formaldehyden-conden-sation product.

The non-ionic surfactants are mainly chosen from amongst the polyglycol ether derivatives of aliphatic or cycloaliphatic alcohols, saturated or unsaturated fatty acids and alkylphenols which can contain 3 to 30 glycol ether groups and 8 to 20 C atoms in the (aliphatic) hydrocarbon radical and 6 to 18 C atoms in the alkyl radical. Other suitable non-ionic surfactants are the water-soluble polyethyleneoxy-adducts onto polypropylene glycol and alkyl polypropylene glycol with 1 to 10 C atoms in the alkyl chain, which adducts contain 20 to 250 ethylene glycol ether groups and 10 to 100 propylene ether groups. The compounds which have been mentioned customarily contain 1 to 5 ethylene units per propylene glycol unit.

The following may be mentioned as examples of non-ionic surfactants: nonylphenol polyethoxyethanols, castor oil polyglycol ethers, polypropylene/polyethylene oxide adducts, tributylphenoxy-polyethoxy-ethanol, polyethyleneglycol and octylphenoxy-polyethoxyethanol. Moreover, fatty acid esters of polyoxyethylene-sorbitan, such as polyoxyethylene sorbitan trioleate, are also suitable.

The cationic surfactants are mainly quaternary ammonium salts which contain at least one alkyl radical having 8 to 22 C atoms as the N-substituent and which have lower, optionally halogenated alkyl radicals, benzyl radicals or lower hydroxyalkyl radicals as further substituents. The salts are mainly present in the form of halides, methylsulfates or ethylsulfates, for example stearyltrimethylammonium chloride or benzyldi( 2-chloroethyl)-ethylammonium bromide.

When preparing the inventive spontaneously dispersible concentrates, special preference is given to phosphoric acid ester tensides, such as:

Tristyryl phenolpolyoxyethylene-18-mono/dimethyl-phosphoric-acid-ester (Soprophor® FL, Rhône-Poulenc);

Nonylphenol-10-polyoxyethylene-mono/dimethylphosphoric-acid-ester (Diphasol® 3873, CIBA-GEIGY);

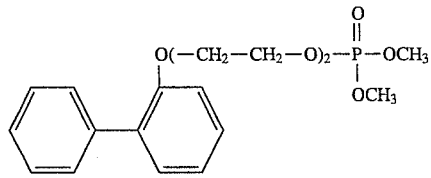

(Tensid 508, CIBA-GEIGY);

Tinovetin® JU (CIBA-GEIGY), a hydroxybiphenyl-10-ethoxy-phosphoric acid ester

Butyl-mono-4-ethoxy-phosphoric acid ester (Zerostat® AT, CIBA-GEIGY), and

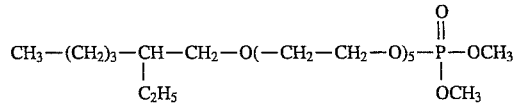

(Zerostat ® AN, CIBA-GEIGY), respectively.

The following compounds may be employed as the pharmaceutically acceptable solvent which acts as the hydrotropic, or coemulsifier, for example: esters of an aliphatic alcohol ($C_3$ to $C_{18}$) with an aliphatic carboxylic acid ($C_{10}$ to $C_{22}$), such as isopropyl laurate, hexyl laurate, decyl laurate, isopropyl myristate and lauryl myristate; hydrocarbons having a straight carbon chain ($C_{12}$ to $C_{32}$) which is substituted by 6 to 16 methyl groups and which can have up to 6 double bonds, examples which may be mentioned being terpenes, such as polymethylbutanes and polymethylbutenes.

Monoesters of ethylene glycol or propylene glycol with an aliphatic carboxylic acid ($C_6$ to $C_{22}$), such as propylene glycol monolaurate and propylene glycol monomyristate.

Esters of an aliphatic alcohol ($C_{12}$ to $C_{22}$) with lactic acid, such as, for example, myristyl lactate or, preferably, lauryl lactate. Monoesters or diesters of glycerol with an aliphatic carboxylic acid ($C_6$ to $C_{22}$), such as, for example, glyceryl caprylate or Miglyol® 812 (which has the structure R—O—$CH_2$—CH(—OR)—$CH_2$—O—R, wherein R is a $C_{8,10}$ acyl) neutral oil (Oleum neutrale). Esters of a poly(2-7)ethylene glycol glycerolether having at least one free hydroxyl group with an aliphatic carboxylic acid ($C_6$ to $C_{22}$), such as, for example, aliphatic alcohols ($C_{12}$ to $C_{22}$), thus, inter alia, dodecanol, tetradodecanol, oleyl alcohol, 2-hexyldecanol and 2-octyldecanol. Esters containing at least one free hydroxyl group, of poly-(2-10)glycol with an aliphatic carboxylic acid ($C_6$ to $C_{22}$), Monoethers of a polyethylene glycol with an aliphatic alcohol ($C_{12}$ to $C_{18}$), such as, for example, polyoxyethylene-($C_{10}$) octylether. Heterocyclic compounds such as 1-methyl-2-pyrrolidon.

Before their application into the spontaneously dispersible concentrates all technical tensides have been cleaned by filtration and by chromatography over aluminum-oxide with an inert solvent as eluent, such as tetrahydrofurane, ethylalcohol or dichlormethane.

Suitable additives for the spontaneously dispersible concentrates according to the invention are vitamins and provitamins [such as, for example, vitamin A (retinoic acid, Tretinoin), retinol, carotenes, tocopherols], and also free fatty acids, such as: valeric acid, isovaleric acid, sorbic acid, isocaproic acid, pelargonic acid, lauric acid, myristic acid, palmitic acid, stearic acid, arachidic acid, behenic acid, hexacosanoic acid, octacosanoic acid, pentadecanoic acid, decenylic acid, undecenylic acid, dodecenylic acid, oleic acid, linoleic acid, linolenic acid, arachidonic acid, erucic acid, etc.

The daily dose required for pharmaceutical administration is 0.001 to 25 mg/kg of body weight, if possible split into 2-3 individual doses. For this purpose, the fatty acid esters of sterols and their phosphatides, or the spontaneously dispersible concentrates with these compounds, can be incorporated into the conventional pharmaceutical preparations and dosage forms, such as coated tablets, tablets, capsules, powders, granules, pellets, solutions, ampuls, emulsions, creams or suppositories together with the customary excipients and/or diluents and stabilizers.

The active substances or mixtures of active substances which form the subject-matter of the invention, and the spontaneously dispersible concentrates which contain these active substances or mixtures of active substances, can be administered to humans orally, by injection (intravenously, subcutaneously or intramuscularly) or in other ways. If they are presented as solid dosage forms for oral administration, this can be in the form of tablets, granules, pellets, powders or capsules, etc. The preparations can contain additives, for example a pharmaceutical excipient, such as a saccharide or cellulose base, a binder, such as starch paste or methylcellulose, a filler, or a disintegrant, etc., with additives being employed which are customarily used in the preparation of medicinal or pharmaceutical formulations. When the active substances or mixtures of active substances according to the invention are administered orally in the form of liquid dosage forms, they can be present in any form selected from amongst aqueous preparations for internal use, from suspensions, emulsions and syrups, etc., and they can also be present in the form of dried preparations which are dissolved or emulsified prior to use.

When the active substances or mixtures of active substances according to the invention are processed in the form of aqueous solutions, suspensions or oily or aqueous emulsions, preferably microemulsions, from the spontaneously dispersible concentrates according to the invention, they can also be injected. However, it is customary to prepare the injection solutions shortly before administration, by dissolving or suspending the extracts or concentrates in aqueous, liquid media, such as sterile water or physiological sodium chloride solution or glucose solution. If required, conventionally used solvents, stabilizers, preservatives and additives for the preparation of isotonic solutions can be added to a preparation for injection. The preparations for injection obtained in this manner are administered intravenously, intramuscularly, subcutaneously or in any other suitable way.

The present invention also relates to pharmaceutical preparations which contain the active substances, or mixtures of active substances, or the spontaneously dispersible concentrates, which have been above described, for controlling the growth of tumour cells. The pharmaceutical preparations according to the invention are those which can be used for enteral (such as oral or rectal) or for parenteral or topical administration to warm-blooded animals, which preparations contain the spontaneously dispersible concentrate on its own or together with a pharmaceutically acceptable excipient.

The dosage of the concentrates according to the invention depends on the warm-blooded species, on the age and on the individual condition, and on the mode of administration. For example, doses in the range of about 0.1 to 50 mg/kg of body weight are administered subcutaneously, and doses in the range of 0.05 to 5 mg/kg of body weight are administered intraperitoneally to warm-blooded animals having a low body weight, such as, for example, mice, rats and hamsters, to achieve an effect of tumour cell destruction.

The oral and rectal forms of the novel pharmaceutical preparations contain between 1 and 95%, preferably between 10 and 95%, and in particular between 20 and 95%, of the spontaneously dispersible concentrate according to the invention. For example, they can be present in unit-type dosage forms, i.e., as coated tablets, micropellets, tablets, suppositories or ampuls and, in particular, as capsules.

Suitable pharmaceutically acceptable excipients for the oral forms are mainly fillers, such as sugars (for example lactose, sucrose, mannitol or sorbitol), cellulose preparations and/or calcium phosphates (for example tricalcium phosphate or calcium hydrogen phosphate), furthermore binders, such as starch paste, with the use of, inter alia, corn starch, wheat starch, rice starch or potato starch, gelatine, tragacanth, methylcellulose, hydroxymethylcellulose, sodium carboxymethylcellulose and/or polyvinylpyrrolidone and/or disintegrants (if desired), such as the above mentioned starches, furthermore carboxymethyl starch, crosslinked polyvinyl-pyrrolidone, agar, alginic acid or a salt thereof, for example sodium alginate.

Examples of suitable flow-control agents are the polyethylene glycols Nos. 200 to 600.

The gelatine capsules, which are still the preferred dosage form for humans, are provided with suitable coatings, concentrated sugar solutions [which can optionally contain gum arabic, talc, polyvinylpyrrolidone, polyethylene glycol and/or titanium dioxide],lacquer solutions (aqueous or those which have been prepared using organic solvents), or enteric coatings of solutions of suitable cellulose preparations, such as microcrystalline cellulose (Acicel™), acetylcellulose phthalate, hydroxy-methylcellulose-phthalate, Metolose®, AQOAT® or a copolymer, such as Eudragit® L 30 D, being used, inter alia.

Pharmaceutical dosage forms for oral use which are particularly suitable according to the invention are two-piece gelatine capsules with a plasticizer, such as glycerol or sorbitol. The soft-gelatine or hard-gelatine capsules and the capsules made of AQOAT™ hydroxypropyl methylcellulose respectively can contain the spontaneously dispersible concentrate according to the invention as a mixture with fillers, such as lactose, binders, such as starch, and/or glidants, such as talc or magnesium stearate, and, if appropriate, together with stabilizers and antioxidants, such as, for example, α-, β- or γ-tocopherol. It may be expedient to employ suitable liquids, such as liquid polyethylene glycols Nos. 200 to 600 as diluents, to which stabilizers and antioxidants can also be added.

For parenteral administration, distilled water is added to the concentrates according to the invention. To the aqueous microemulsion for injection which then forms, there can be added viscosity-increasing substances, for example Na-carboxymethyl-cellulose, sorbitol, mannitol and/or dextran, and if appropriate also stabilizers and antioxidants.

The pharmaceutical preparations for parenteral administration preferably contain between 0.1 and 60%, especially between 1 and 40%, of the spontaneously dispersible concentrate according to the invention.

Suitable preparations for topical use, which are particularly suitable for the prophylaxis and the treatment of cancers of the skin, are, for example, creams, ointments, pastes, foams, tinctures and solutions, which contain between 0.001 and 70% of the concentrate according to the invention.

Oily bases which are used for creams and oil-in-water emulsions which contain more than 50% water, are mainly fatty alcohols, for example lauryl alcohol, cetyl alcohol or stearyl alcohol, waxes of liquid to solid consistency, for example isopropyl myristate, wool wax or beeswax and/or hydrocarbons, such as, for example, petroleum jelly (petrolatum) or paraffin oil. Substances which are mainly suitable for emulsifying these oily bases are surface-active, pharmaceutically acceptable substances having predominantly hydrophilic properties, such as, for example, nononic emulsifiers, in particular fatty acid esters of polyalcohols or ethylene oxide adducts (such as polyglycerol fatty acid esters or polyethylene sorbitan fatty acid esters) having an HLB-value of less than 8. Additives which are added to the water phase are, inter alia, agents which prevent desiccation of the creams, for example polyalcohols, such as glycerol, sorbitol, propylene glycol and/or polyethylene glycols Nos. 200–600, and furthermore preservatives, odor-imparting substances, etc.

Ointments are water-in-oil emulsions which contain up to 70%, but preferably between 20 and 50%, water or aqueous phases. Substances which are suitable as the lipid phase are mainly hydrocarbons, for example petroleum jelly, paraffin oil and/or solid paraffins, which contain hydroxy compounds suitable for improving the water-binding capacity, for example fatty alcohols or esters, such as cetyl alcohol or wool wax alcohols.

In some cases, emulsifiers having an HLB-value of 8 to 16, such as, for example, sorbitan fatty acid esters (such as sorbitan isostearol) are also added. Additives which are added to the water phase are, inter alia, humectants, such as polyalcohols (glycerol, propylene glycol, sorbitol and/or polyethylene glycols No. 200, 400, 600); and furthermore preservatives, odor-imparting substances, etc.

Fatty ointments are anhydrous and chiefly contain hydrocarbons as the base, for example paraffin, petroleum jelly and/or liquid paraffins; moreover natural or partially-synthetic fats, such as, for example, coconut fatty acid triglyceride, furthermore: fatty acid partial esters of glycerol, such as, for example, the fatty alcohols, emulsifiers and/or additives which increase the water-absorption capacity, all of which have been mentioned in connection with the ointments.

Pastes are creams and ointments containing powder constituents which absorb secretions, such as, for example, metal oxides (such as titanium oxide or zinc oxide), and furthermore talc and/or aluminum silicates whose task it is to bind any moisture or discharge which may be present.

Foams are administered from pressurized containers and are oil-in-water emulsions of the spontaneously dispersible concentrates according to the invention which are present in aerosol form, with halogenated hydrocarbons (such as, for example, lower chloro-fluoroalkanes; such as dichloro-difluoromethane and dichloro-tetrafluorethane) being added as propellants. Other substances which may be added are the customary additives, such as preservatives, etc.

The present invention also relates to the use of the active substances, mixtures of active substances and spontaneuosly emulsifiable concentrates according to the invention for inhibiting the growth of tumour cells or as prophylactic agents against oncoses in humans and animals, administration preferably being carried out in the dosage forms which correspond to the pharmaceutical preparations described above. For use as dietary foods and as food additives, the optimum compositions must be established for every individual case.

Figure 1:
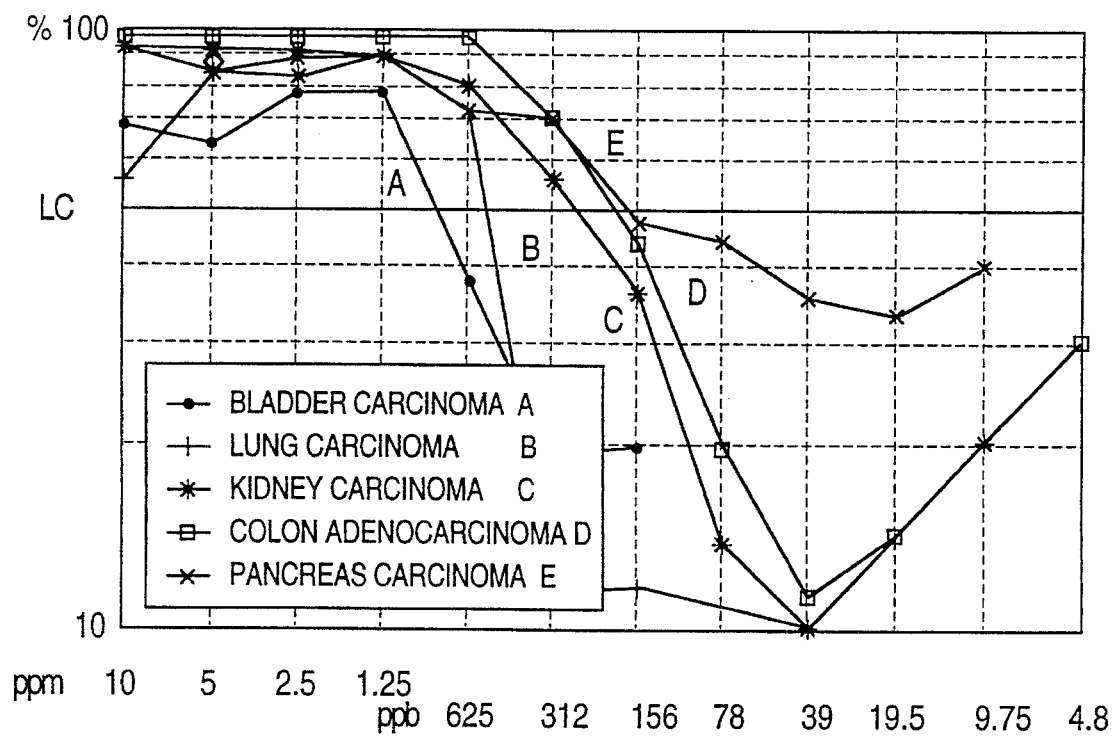
FIGS. 1 and 2 depict the in vitro cytotoxicity of ergosterol-all trans-retinate and ergosterol-undecenoate, respectively.
Figure 2:
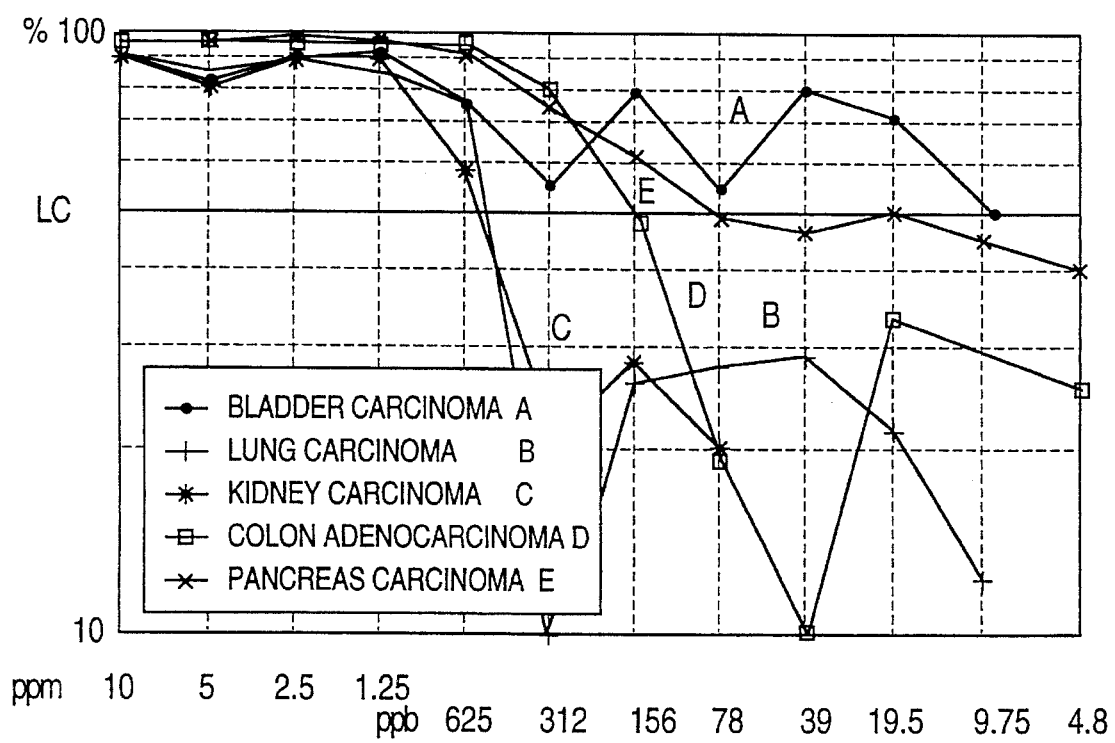
Figure 3:
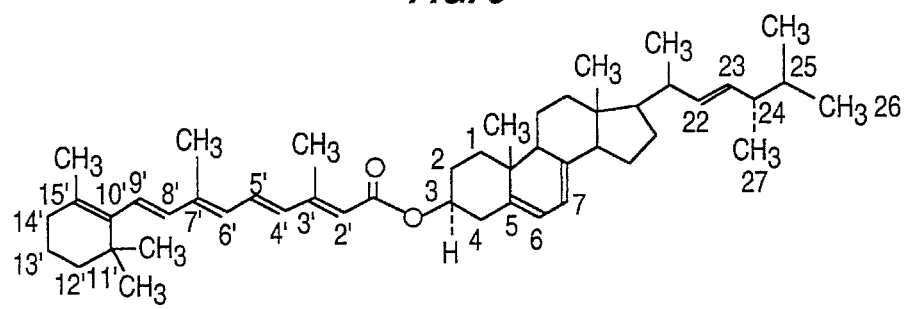
FIG. 3 shows the structure and NMR spectrum for ergosterol-3β-all trans-retinate.
Figure 4:
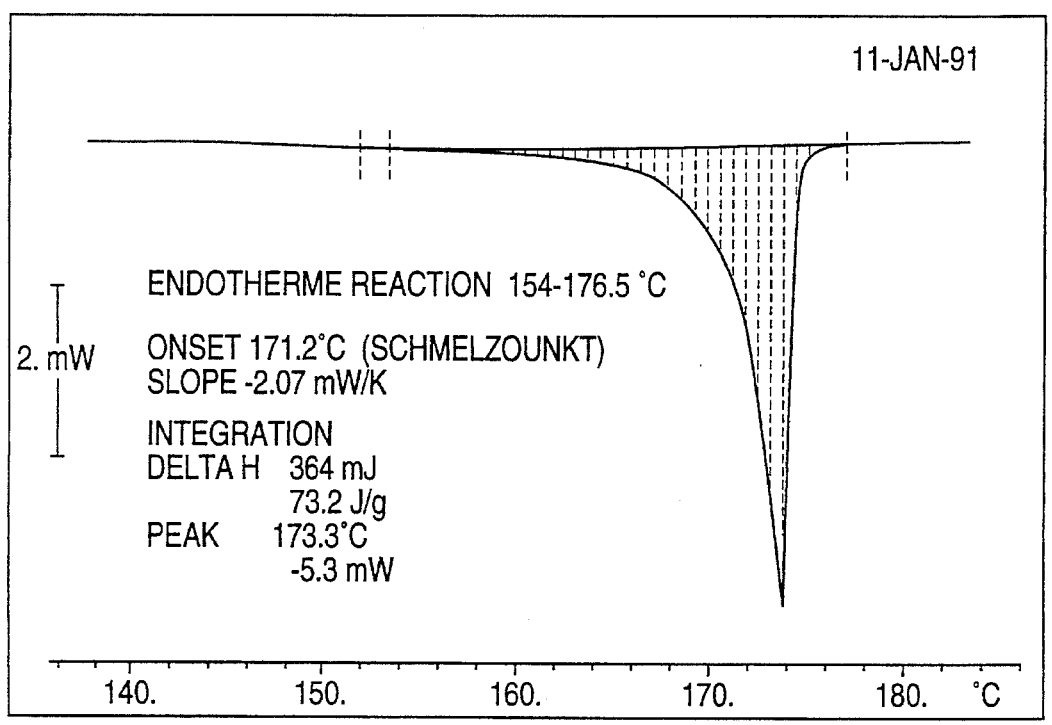
FIGS. 4 and 5 depict the density scanning calorimetry showing the melting range for stigmasterol-1,2-dipalmitoyl-glycero-phosphatide and stigmasterol-1,2-dipalmitoyl-glycerothiophosphatide, respectively.
Figure 5:
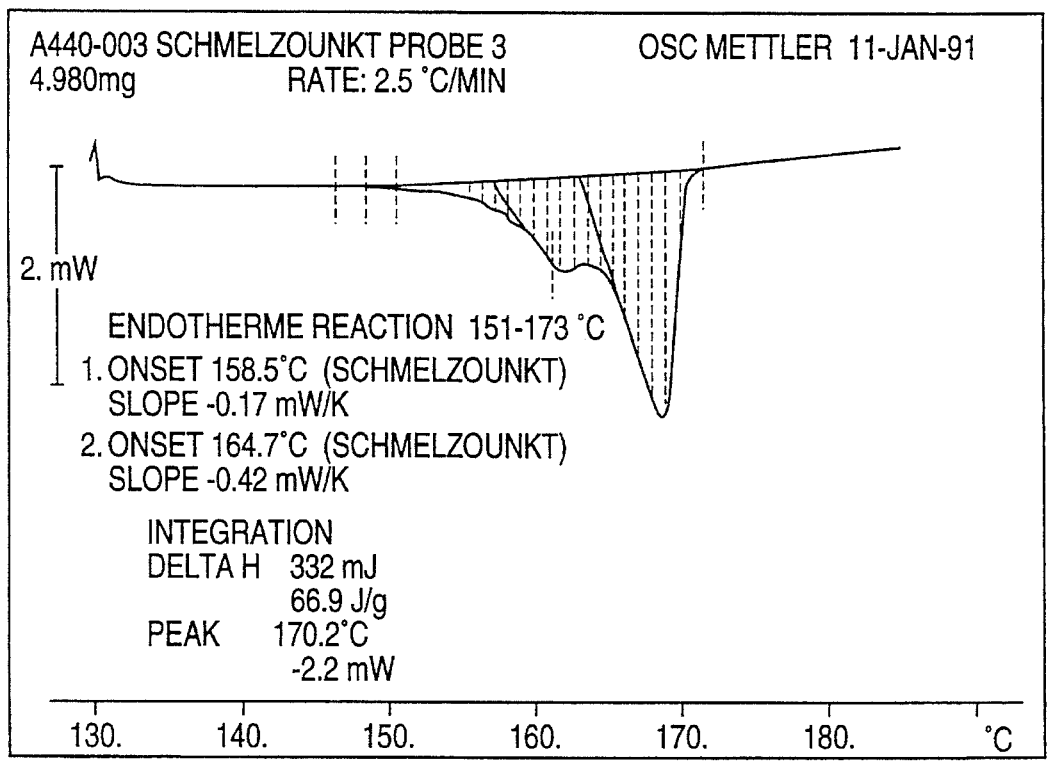

PROCESSING EXAMPLES FOR STEROLESTERS AND STEROPHOSPHATIDES OF THE FORMULAE (I) TO (XV) ACCORDING TO THE INVENTION

1. Process for the preparation of ergosta-5,7,22-trien-3-ol-dodecenoate.

2 g of trans-2-dodecenoic acid (Mw 198.31) and 1.8 g thionylchloride in 300 ml tetrahydrofurane are refluxed for 2 hours. Then 150 ml tetrahydrofurane are distilled off in vacuo. 3.97 g ergosterol (ergosta-5,7,22-trien-3-ol) and 0.5 g dimethylformamide are added. The reaction mixture is being refluxed at 70° C. for further 2 hours. The solvent is distilled off on a Rotavapor and the residue is recrystallized in acetonitrile/acetone (50/50).

Ergosterol-trans-2-dodecenoate is obtained in the form of crystals having a melting point of 86.6° to 91.1° C.

The following compounds are prepared in analogous manner:

| | | |
|---|---|---|
| Ergosterolcrotonate | mp: | 150 to 151.6 °C. |
| Ergosterolcapryloate | mp: | 97.9 °C. |
| Ergosterol-10-undecenoate | mp: | 75.8–76.2° C. |
| ERGOSTEROL-10-UNDECENOATE | IR: | 2932 cm$^{-1}$ v(CH) |
| | | 2871 cm$^{-1}$ v(CH) |
| | | 1722 cm$^{-1}$ v(C=O) Ester |
| | | 1639 cm$^{-1}$ v(C=O) |
| | | 1457 cm$^{-1}$ δ(CH) |
| | | 1371 cm$^{-1}$ δ(CH$_3$) |
| | | 1186 cm$^{-1}$ v(C=O) |
| | | 983 cm$^{-1}$ δ(CH) } |
| | | 914 cm$^{-1}$ Vinyl } |
| Ergosterollaurate | mp: | 86.5° C. |
| Ergosterolpalmitate | mp: | 99.5° C. |
| Ergosterololeate | RI | (Refractory Index): 1.50716 |
| Ergosterollinoleate | RI: | 1.50970 |

|                     | UV: | λmax. 253.0 nm |
|---------------------|-----|----------------|
| Ergosterollinolenate | RI: | 1.51254        |

2. Process for the preparation of Stigmasterol-all trans-retinate.

To a solution of 70 ml toluene containing 600 mg all trans retinoic acid and 50 mg dimethylformamide 360 mg oxalylchloride are added dropwise at a temperature of 5° C. After standing at room temperature for 4 hours, half the amount of the solvent is distilled off. To the rest of the solution 650 mg stigmasterol and 50 mg dimethylaminopyridine in 30 ml toluene are being added. The reaction mixture is refluxed at 100° to 110° C. for further 2 hours. The solvent is distilled off on a Rotavapor, and the residue is chromatographed on a silicagel column; eluent n-hexane/ethyl acetate 9:1. Stigmasterol-all trans-retinate is obtained, with a melting point of 89° C. UV absorption λmax.358.5 nm.

The following compounds are prepared in analogous manner:

| Ergosterol-all trans-retinate | mp: | 132.4 to 133.6 |
|---|---|---|
|  | UV: | λmax. 360,0 nm |
| ERGOSTEROL-all trans-RETINATE | IR: | 2958 $cm^{-1}$ v(CH) |
|  |  | 2871 $cm^{-1}$ v(CH) |
|  |  | 1701 $cm^{-1}$ v(C = O) |
|  |  | 1608 $cm^{-1}$ v(C = C) |
|  |  | 1583 $cm^{-1}$ v(C = C) |
|  |  | 1457 $cm^{-1}$ v(CH) |
|  |  | 1239 $cm^{-1}$ v(C = O) |
|  |  | 1153 $cm^{-1}$ v(C = O) |
|  |  | 1016 $cm^{-1}$ v(C = O) |
|  |  | 970 $cm^{-1}$ trans (C = C) δ(CH) |
| β-Sitosterol-all trans-retinate | UV: | λmax 344.5 nm |
| Cholesterol-all trans-retinate | UV: | 354.5 nm |
| Stigmasterol-13-cis-retinate | UV: | 348.0 nm |
| Ergosterol-13-cis-retinate | UV: | 346.0 nm |
| β-Sitosterol-13-cis-retinate | UV: | 368.5 nm |
| Cholesterol-13-cis-retinate | UV: | 345.5 nm |
| Ergosterol-linolenate | UV: | 252.2 nm |
| Stigmasterol-aracidonate | UV: | 251.8 nm |
|  | RI: | 1.51320 / 20° C. |

Data of the NMR-analysis of Ergosterol-all trans-retinate are given in the technical annexure 1/2.

3. Preparation of Stigmasterol-azafrinate

To a solution of 80 mg azafrinate, formula (XXI) [process for preparing this compound vide Helv. Chim.Acta 58 (1975) 1722 to 1727 and Helv.Chim Acta 65 (1982) 353–354] in 50 ml chloroform 65 mg N,N'-carbonyldiimidazole are added. The mixture is left standing for 12 hours at room temperature, then 40 mg stigmasterol are added. After further 12 hours at a temperature of 30° C. the solvent is distilled off and the residue diluted in 50 ml ethyl acetate. The solution is washed once with 1/10N hydrochloric acid and once with 1/10N sodium hydroxide and then the solvent is distilled off. The residue is chromatographed on a silicagel column; eluent: n hexane/ethyl acetate 9:1. Stigmasterol-azafrinate is obtained with a UV absorption λmax. of 429.5 nm. In the same way the following compounds are prepared:

| β-Estradiol-3,17-di-10-undecenoate | RI: | 1.4816 |
|---|---|---|
|  | UV: | 232.8/276.0 nm |
| β-Estradiol-3,17-dioleate | RI: | 1.5058 |
|  | UV: | 232.0/280.0 nm |
| β-Estradiol-3,17-di-all trans-retinate | UV: | 354.5/371.0 nm |
| β-Estradiol-3-benzoate-17-undecenoate | UV: | 247.6 nm |
| β-Estradiol-3-benzoate-17-all trans-retinate | UV: | 354.5 nm |

4. Process for preparing Stigmasterol-1,2-dipalmitoyl-glycero-phosphatide and Stigmasterol-1,2-dipalmitoyl-glycerothiophosphatide

1,2-dipalmitoyl-glycero-3-H-phosphonate-triethylammonium salt is prepared according to the method of I. Lindth and J. Stawinski in J. Org. Chem 54, 1338–1342 (1989): "Synthesis of glycerophospholipids and their analogues via H-phosphonate".

The reaction product can be used for the next chemical step without any intermediary cleaning operation by chromatography. 600 mg of the reaction product and 600 mg stigmasterol are dissolved in pyridine and brought to dryness in vacuo. The residue is again dissolved in 15 ml pyridine. After adding 0.2 ml pivaloylchloride, this solution is stirred 30 minutes in dry athmosphere. After further adding 0.1 ml pivaloylchloride the solution is again stirred for 30 minutes at room temperature.

The reaction solution is then divided into two parts: To the first part of this solution 150 mg jodine, dissolved in 2 ml pyridine-water 98:2, are added. After 30 minutes stirring at 20° C. the reaction mixture is poured in 50 ml chloroform. This solution is washed once with 20 ml 5% sodium-bisulfit-solution and twice with 20 ml water. After separation the chloroform-phase is distilled off to dryness on a Rotavapor.

To the other part of the solution 150 mg sulfur in 2 ml pyridine-toluene 1:1 are added. The solution is stirred for 3 hours at a temperature of 20° C. 50 ml chloroform are added and then the solution is washed twice with 20 ml water. After the separation has taken place the chloroform-toluene-phase is being distilled off to dryness on a Rotavapor.

The two raw products are chromatographed on a silicagel column with chloroform/hexane 2:1 and 8:1 as eluent.

The following products are obtained: Stigmasterol-1,2-dipalmitoyl-glycerophosphatide, with a melting point of 171.6° C. and Stigmasterol-1,2-dipalmitoyl-glycero-thiophosphatide, with a melting point of 168° C.

In an analogous way ERGOSTEROL-1,2-dipalmitoyl-glycero-phosphatide is obtained as clear waxy crystals. The melting point cannot be determined.

N.B.:

UV spectra measured on a spectrophotometer Shimadzu UV-160A

RI=refractory index measured on a DUR-refractometer Schmidt+Haensch, Berlin

IR=Infra red spectra measured on a spectrophotometer Perkin Elmer 983G NMR-analytical data assessed on a Bruker AM-360 spectrometer Rf-values of inventive compounds which are being prepared according to the examples 1 to 4:

1% solution in $CH_2Cl_2$, applied in bands 2 cm/2 μl.
Linomat III CAMAC 10 cm run
UV 366 after 1:1 $H_2SO_4$/MeOH 2 min. 120° C.

| SYSTEM COMPOUND | 1 | 2 | 3 | 4 | 5 | 6 | 7 |
|---|---|---|---|---|---|---|---|
| ERGOSTEROL-C 8:0 | — | 0.17 | 0.32 | 0.77 | — | 0.81 | — |
| ERGOSTEROL-C 12:0 | 0.06 | 0.14 | 0.29 | 0.73 | 0.89 | 0.74 | 0.57 |
| ERGOSTEROL-C 16:0 | 0.07 | 0.16 | 0.32 | 0.75 | 0.92 | 0.82 | 0.58 |
| ERGOSTEROL-C | 0.08 | 0.18 | 0.35 | 0.80 | 0.92 | — | 0.63 |

-continued

1% solution in CH₂Cl₂, applied in bands 2 cm/2 µl.
Linomat III CAMAC 10 cm run
UV 366 after 1:1 H₂SO₄/MeOH 2 min. 120° C.

| 18:1 | | | | | | | |
|---|---|---|---|---|---|---|---|
| ERGOSTEROL-all trans-RETINATE | 0.07 | 0.17 | 0.42 | 0.00 | 0.91 | 0.87 | 0.73 |
| β-ESTRADIOL-3, 17-BIS-UNDECENOATE | 0.00 | 0.00 | 0.04 | 0.18 | 0.71 | 0.29 | 0.07 |

Explanation:
System 1 Plate Merck Art. 5716 petrolether/diethylether 98:2
System 2 Plate Merck Art. 5715 petrolether/diethylether 97:3
System 3 Plate Merck Art. 5715 cyclohexane/ethylacetate 97:3
System 4 Plate Macherey Nagel RP 18 Art. 811'071 petrolether/diethylether 95:5
System 5 Plate n hexane/t.butylmethylether/acetone 90:5:5
System 6 Plate petrolether/cyclohexane/ethylacetate/H₂O 48:48:3:1
System 7 petrolether/diethylether 97:3

| SYSTEM COMPOUND | 1 | 2 | 3 | 4 | 5 |
|---|---|---|---|---|---|
| ERGOSTEROL-C 18:2 | 0.76 | 0.39 | 0.60 | 0.92 | 0.79 |
| ERGOSTEROL-C 18:3 | 0.78 | 0.40 | 0.65 | 0.92 | 0.80 |
| β-Estradiol-3,17-DI-UNDECENOATE | 0.38 | 0.10 | 0.15 | 0.75 | 0.30 |
| β-Estradiol-3.17-DI-OLEATE | 0.42 | 0.22 | 0.20 | 0.83 | 0.38 |

EXPLANATION:
SYSTEM 1 Plate RP 18 MN petrolether/cyclohexane/EtAc/H₂O 48:48:3:1
SYSTEM 2 Plate SM cyclohexane/ethylacetate 97:3
SYSTEM 3 Plate SM petrolether/diethylether 97:3
SYSTEM 4 Plate RP 18w MN n-hexane/t.BME/acetonitrile 90:5:5
SYSTEM 5 Plate RP 18w MN petrolether/diethylether 95:5
N-B.: SM Plate Merck Art. No. 5715 RP18 MN(w) Art. Macherey Nagel Nr. 811'071
Rf.-Values with normal chromatography
n-hexane/ethylacetate 90:10:

| β-Estradiol-diundecenoate | 0,37 |
|---|---|
| β-Estradiol-dioleate | 0,48 |
| Ergosterol-all trans-retinate | 0,88 |
| Ergosterol-linoleate | 0,82 |
| Ergosterol-linolenate | 0,96 |
| Stigmasterol-glycero-phosphatide | 0,88 |
| Stigmasterol-glycero-thiophosphatide | 0,94 |
| Plate Merck Art. No. 5715 | |

DEMONSTRATION OF THE SPREADING AND PERMEATION CAPACITY OF THE INVENTIVE CONCENTRATES AND OF EMULSIONS PREPARED WITH SUCH CONCENTRATES

Method: TL-Plate 0.25 mm Silicagel 60F254 Merck Art. No. 11'798 with concentration zone.
Eluent: PBS Dulbecco's without Ca and Mg (=Ringer solution or physiological sodium chloride solution, buffered)

| Rf.-Values | |
|---|---|
| CHOLESTEROL | 0 |
| ERGOSTEROL | 0 |
| ERGOSTEROL-C 11:1 | 0.38 |
| ERGOSTEROL-C 11:1-EMULSION | 0.60 |
| ERGOSTEROL-all trans-RETINATE | 0.65 |
| UVITEX CF conc./ethanol | 0.49 |
| UVITEX CF conc.-EMULSION | 0.62 |

P.S.: 0,1% substance, dissolved in chloroform
Emulsion: 1'000 ppm active substance = 1 mg/ml.

The above indicated Rf.-Values illustrate the behaviour of the inventive concentrates in cell colonies and, more specifically, at the membrane of tumour cells. The reduced surface tension of the concentrates, with values of 30 to 32 mN/m, the small size of the generated micromicelles (1 to 1.2 nm radius!) as well as the low viscosity of the emulsion are all factors which influence the diffusion and the spreading in the cell plasma in a very favourable manner. This factors result in greatly enhanced bioavailability and effectiveness.

Composition examples of spontaneously dispersible agents which contain as substances possessing antitumour activity sterolesters and/or sterolphosphorous compounds according to the formulae (I) to (XV):

a) 0.5 to 25% by weight of one or several of the sterolesters and/or sterolphosphorous compounds of the formulae (I) to (XV) 0.1 to 40% by weight of isopropylmyristate, isopropylpalmitate or Miglyol® 812 (Dynamit Nobel)
20 to 45% by weight of emulsifier mixture Diphasol® 3873 (CIBA- GEIGY)
20 to 45% by weight of Invadin® JFC 800% (CIBA-GEIGY)

b) 0,5 to 25% by weight of one or several of the sterolesters and/or sterolphosphorous compounds of the formulae (I) to (XV)
0,1 to 40% by weight of isopropylmyristate, isopropylpalmitate or Miglyol® 812 (Dynamit Nobel)
20 to 45% by weight of Invadin® JFC 800% (CIBA-GEIGY)
20 to 45% by weight of Soprophor® FL (Rhône-Poulenc)

Miglyol® 812 is a neutral oil (oleum neutrale) of Dynamit Nobel, which is a triglyceride of the coconut acid ($C_8$ to $C_{10}$).

Diphasol® 3873 (CIBA-GEIGY) is a surfactant mixture consisting of the following two compounds (50:50):

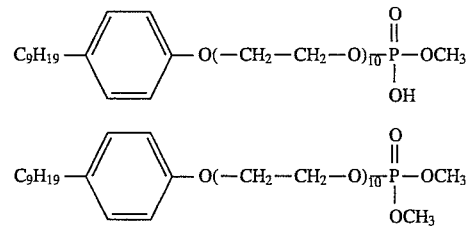

Invadin® JFC 800% (CIBA-GEIGY) is a tert. octylphenylpolyoxyethylene-ether with 9 to 10 oxyethylene groups Soprophor® FL (Rhône-Poulenc) is a tristyrylphenolpolyoxyethylene-18-mono/dimethyl-phosphor acidester.

Example for the pharmaceutical production of a system's preparation containing the inventive concentrates in the form of "multiple units".

a) Granulation (granules and pellets)

| Metolose ® 90 SH-4000 (Shin-Etsu Chemical) | 90.0 g |
|---|---|
| Avicel ® PH-101 | 80,3 g |
| inventive CONCENTRATE | 139,4 g |
| Aerosil ® 200 | 80,3 g |
| | 390.0 g |

Granulation in the high speed mixer or the fluidized bed, with the addition of 110 g ethanol, sieving on a 18 to 42 mesh screen with crushing, drying for 24 h at 40° C.

b) Enteric and sustained release coating
In the fluidized bed with AQOAT® AS-HG (Shin-Etsu Chemical) and Talc c) Composition of finished granules or micropellets

| Core Material | 44% by weight |
|---|---|
| Inventive CONCENTRATE | 25% by weight |
| Enteric coating | 31% by weight |
| | 100% |

N.B. The pellets or granules according to a) can also be filled without prior coating into capsules which are made of AQOAT™ (HPMC-AS-M or HPMC-AS-N), have been sealed with acetone/ethanol 1:1 and can thus perform the functions of pH-control and slow release.

BIOLOGICAL ASSAYS

The antitumour activity of spontaneously dispersible concentrates containing active substances prepared according to the examples No. 1 to 4 is confirmed by the following test results:

1. In-vitro assays using suitable tumour cell lines

A biological assay system using microtiter plates and serial dilutions has been developed. Batches of $10^4$ tumour cells per ml were set up in culture medium RPMI 1640 and inactivated with 10% of fetal calf serum (GIBCO); they are spread at a density low enough to enable them to grow during the assay, in so-called non-confluent monolayers. Samples are added after 6 to 24 hours, with 100 µl per row, to which 100 µl of medium are added in the first well. Half of this mixture is withdrawn, transferred into the next well and again treated with 100 µl of medium, etc. This results in an n½ geometrical serial dilution.

In the plaque assay, the samples are incubated at 37° C. for 3 to 5 days under 3½% of $CO_2$. They are then stained and fixed using 0.1% crystal violet (Fluka, Buchs) in a solution of 70% of methanol, 1% of formaldehyde and 29% of water. The samples are evaluated under the microscope, magnification 300×. The greatest cytotoxic dilution is determined. The samples can also be evaluated quantitatively by means of scanning and absorption measurement in a spectrophotometer.

2. Evaluation of the results.

Concentrates with 1% active substance-content

| TUMOR LINIE PREPARATION | TSA: Spontaneous murine adenocarcinoma In dilution effective up to 1: 16 h | (dilution calculated on the active substance content) 40 h |
|---|---|---|
| C 18:2-ERGOSTEROL | 2'000'000 | 16'000'000 |
| STIGMASTEROL-AZAFRINATE | 28'600'000 | 28'600'000 |
| ERGOSTEROL-all trans-RETINATE | 800'000 | 1'600'000 |
| STIGMASTEROL-GLYCERO-PHOSPHATIDE | 400'000 | 1'600'000 |
| STIGMASTEROL-GLYCERO-THIOPHOSPHATIDE | 10'000'000 | 20'000'000 |
| β-ESTRADIOL-3,17-OLEATE | 20'000'000 | 40'000'000 |

TSA: murine adenocarcinoma (spontaneous cancer of the breast of the mouse), supplied regularly by Prof. Guido Forni, Istituto di Microbiologia, Università degli Studi di Torino, Scuola di Medicina.

The action of a spontaneously dispersible concentrate containing ERGOSTEROL-LINOLEATE (ERGO-C 18:2, formulated as standard emulsion with 1'000 ppm sterolester) against human leucocytes was the following:

| DILUTION | 24 h | 4 days | 5 days |
|---|---|---|---|
| 1:20 | all cells dead | all cells lysed | — |
| 1:80 | all cells dead | all cells lysed | — |
| 1:200 | R B C lysed | R B C lysed | — |
| 1:400 | R B C lysed Leucocytes o.k.. | all cells lysed | — |
| 1:1'000 | all cells o.k.. | Leucocytes o.k.. | Leucocytes o.k. |
| 1:5'000 | all cells o.k.. | Leucocytes o.k. | Leucocytes o.k. |
| 1:20'000 | all cells o.k. | Leucocytes o.k. | Leucocytes o.k. |

RBC=Red blood cells, erythrocytes.
Proof of membrane-penetration at the single tumour cell.

It can be shown with light microscopy—and also with Laser scanning microscopy, that few hours after incubation there is forming a halo of vacuoles around the nucleus of the cell Example: Py6-cells of 3T3-mice=polyoma transformed fibroblast cells; thinly disseminated, medium concentration (=dilution) of the active-substance containing concentrates.

The analytical demonstration that these vacuoles in fact contain the sterolester active substances is quite clear and unequivocal: it involves cleaning the incubated tumour cells, extracting the cell plasma with 1% SDS, centrifuging, mixing the supernatant with a 0.05%-solution of Uvitex™ CF conc. (CIBA-GEIGY) in acetone/water (85:15). The STEROLESTERS according to the invention extinguish the fluorescence in the longwave UV-segment which is normally occasioned by the marker Uvitex™ CF conc. The thin-layer plate shows blue coloring.

UV-scanning at 366 nm. Microdialysis by means of capillary zone electrophoresis and laser induced flurescence detection (EUROPHOR IRIS 2000).
Functional investigations.

Phagocytosis—and Respiratory Burst Tests were conducted with a 0,25%-concentrate of ERGOSTEROL-all trans-RETINATE. The evaluation was made with fresh human peripheric blood, heparinized, against *Escherichia coli* bacteria. Analysis on the Flow cytometer (FACS). It clearly became apparent that the intracellular processes are dose-dependent. This leads to the indirect conclusion that ERGOSTEROL-all trans-RETINATE is taken up by the cells. (Assays conducted by ANAWA LABORATORIES S.A., Wangen/ZH; Dr. Peter Joller; direct measurement not yet possible on account of extreme dilution below the limit of detection).

Tests with human tumour cell lines

BATTELLE INSTITUTE, Frankfurt, FRG. (Dr. Matthias GIESE) assessed the cytotoxic effect on various selected cell lines of solid human tumours, which grow relatively slowly. The assay was conducted with 2%-concentrates (by weight) of:

A ERGOSTEROL-10-UNDECENOATE (ERGO-C 11:1)

B ERGOSTEROL-all trans-RETINATE with the following tumour cell lines (provided by the German Cancer Research Center, DKFZ, Heidelberg, FRG):

1 EJ28: carcinoma of bladder

2 LX-1: carcinoma of lung

3 KTCTL-1M: carcinoma of kidney

4 CX-1: adenocarcinoma of colon

5 DAN-C: carcinoma of pancreas

The following biological response modifiers (BRM) were used as controls:

a rhu Interferon-Gamma (Biozol, BRD)

b rhu Tumor-Necrosis Factor Alpha (Biozol, BRD)

Results are given in dilution series and using the $IC_{50}$-values as indicator. Incubation of the cells for 24 h, and 72 h respectively, at 37° C.; vitality staining after 3 and 14 days. Testing range $1:10^6$ to $1:10^9$, calculated on the active substance content.

Smaller differences only between the individual cell lines became apparent, as well as relatively feeble differences between the two concentrates. The $IC_{50}$-values are centered in the dilution range $1:10^7$.

In summary, the findings of the tests demonstrate clearly and throughout a cytotoxic effect on the tumour cells and not merely a cytostatic effect.

The strongest cytotoxic effect was shown for ERGOSTEROL-10-UNDECENOATE (ERGO-C 11:1) against the LX-1 cell culture. The control substances BRM, however, showed no measurable effect on any of the 5 cell lines included in the assay.

On the other hand, comparable antitumoral activity could be obtained with the following concentrates, containing:
ERGOSTEROL-OLEATE (ERGO-C 18:1)
ERGOSTEROL-LINOLENATE (ERGO-C 18:3)
ERGOSTEROLESTER-MIXTURE (10 different esters)
STIGMASTEROL-GLUCOSIDE/PHOSPHATIDE-MIXTURE The following graphical representations summarize in figures No. 1 and 2 the results for the first two concentrates.

IN-VITRO ASSAYS CONDUCTED BY THE NATIONAL CANCER INSTITUTE, BETHESDA.

Figure 6:
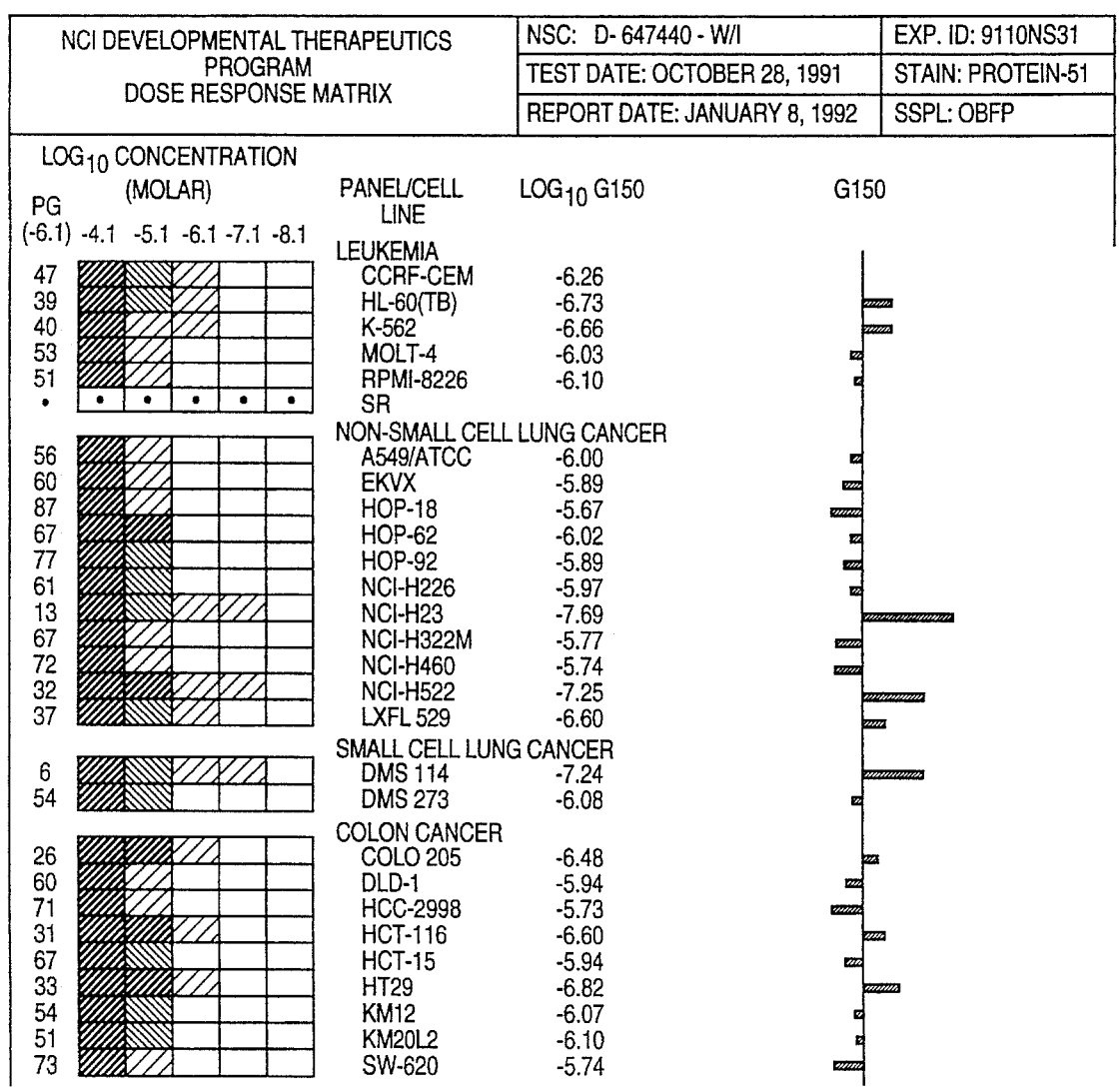
FIGS. 6 and 7 show the dose response matrix of ergosterol- 10-undecenoate against various tumor cell lines in studies conducted by the National Cancer Institute.
Figure 7:
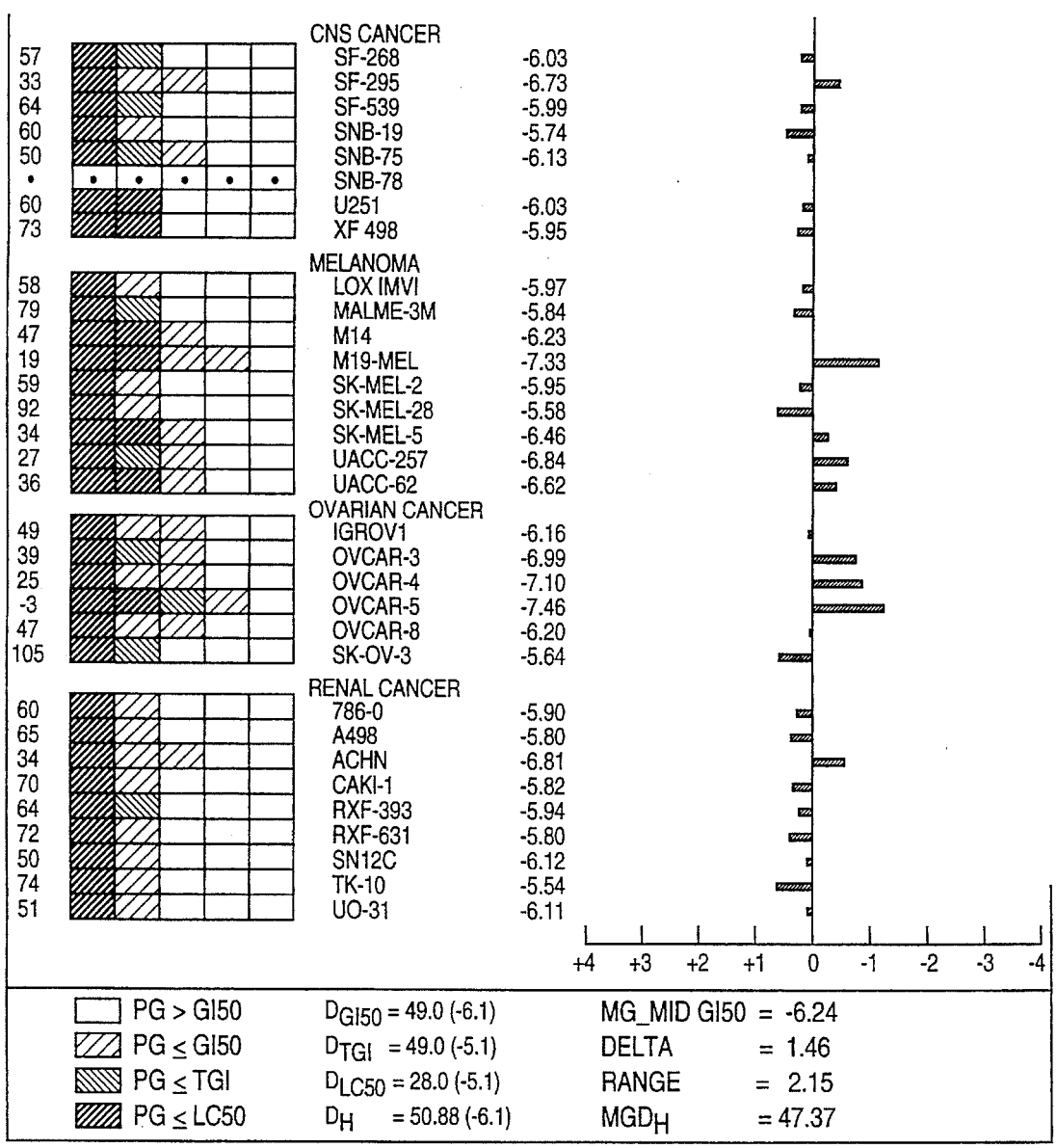
Figure 8:
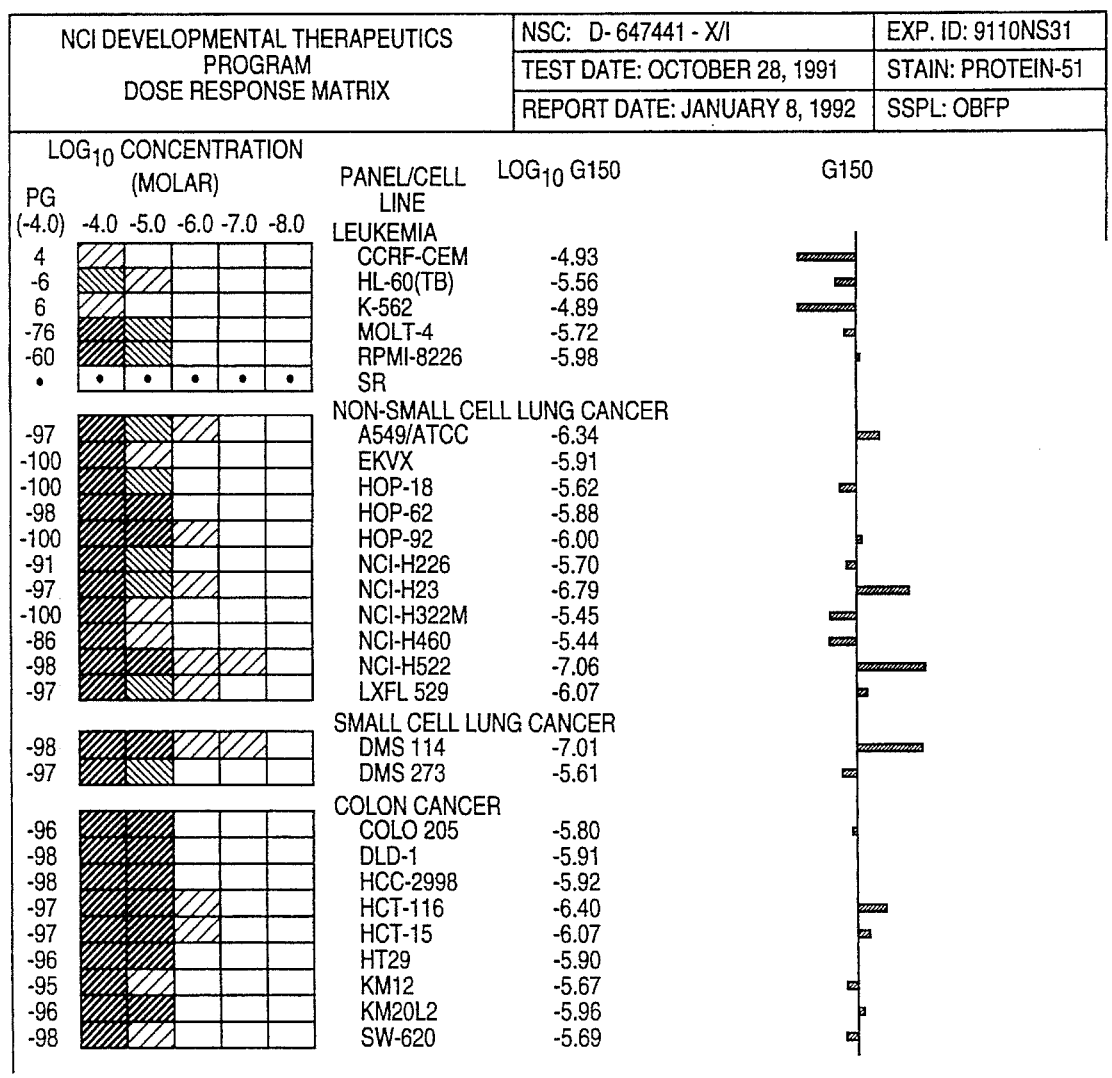
Figure 9:
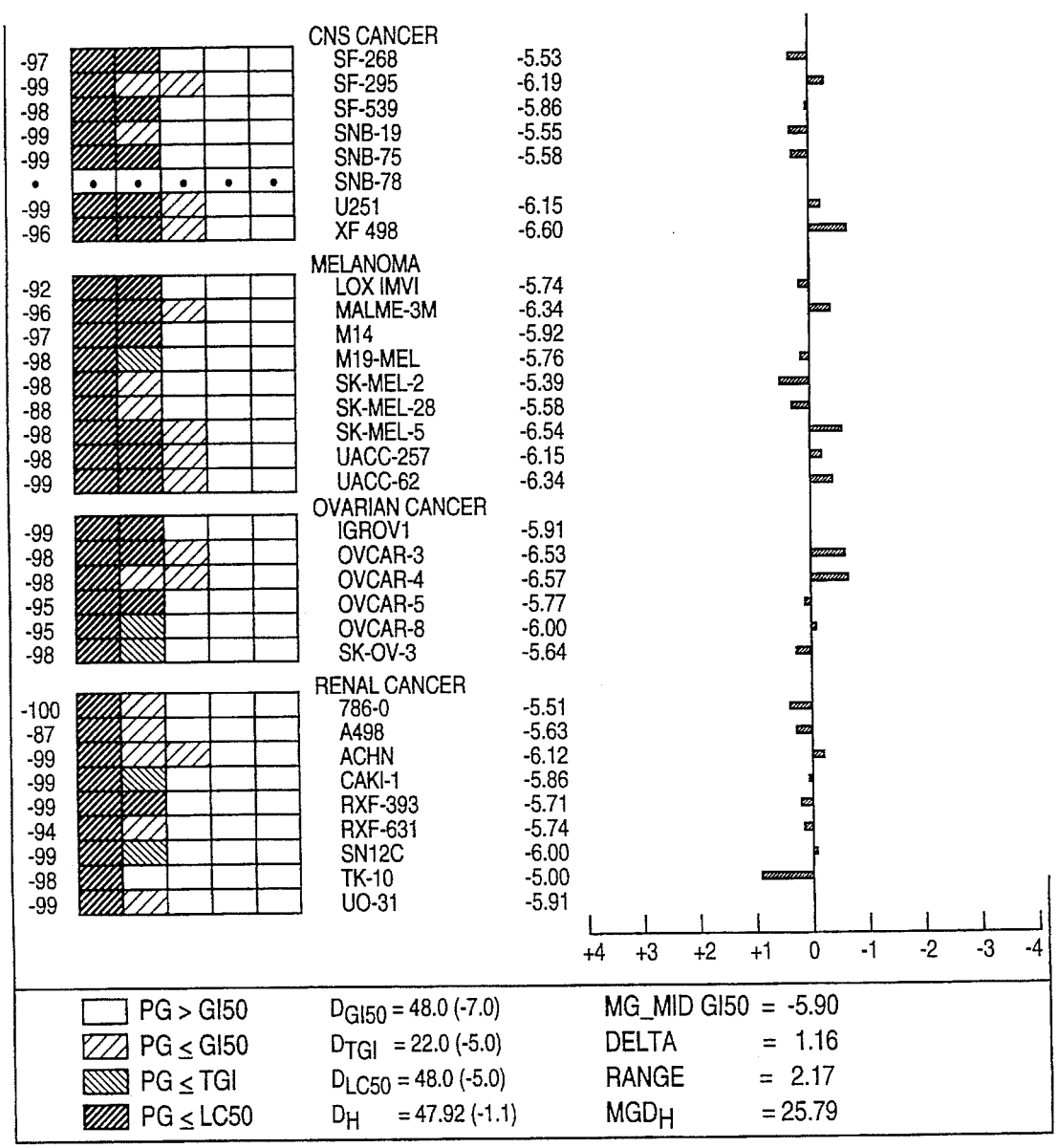

Broad systematic tests conducted by the NCI under their Developmental Therapeutics Program with 60 different cell-lines of human tumours covered 8 PANELS:
Leukemia
Non-small cell Lung Cancer
Small cell Lung Cancer
Colon Cancer
CNS Cancer
Melanoma
Ovarian Cancer
Renal Cancer The following measuring rods were applied:
PG (Percentage Growth)
Dose-Response-Curves
Mean Graphs FIGS. 6 through 9 render the overall results in graphical and statistical summaries for
ERGOSTEROL-10-UNDECENOATE-CONCENTRATE and
ERGOSTEROL-all trans-RETINATE-CONCENTRATE The principal result of the extensive assessment by NCI is quite comparable to the findings reached by BATTELLE INSTITUTE, namely that the INVENTIVE CONCENTRATES not only show an anti-proliferation effect, i.e. a growth inhibition, but a true and general cytotoxicity. This is particularly marked with those cell lines which possess short doubling times and are thus relatively more sensitive to antitumour agents than the slower growing (solid) tumour lines.

Cf. also: Michael R. Boyd: Status of the NCI Preclinical Antitumor Drug Discovery Screen, PPO updates, Vol. 3, October 1989, Number 10.

Anne Monks et al.: Feasibility of a High-flux Anticancer Drug Screen using a diverse Panel of cultured human Tumor Cell Lines. Journal of the National Cancer Institute, Vol. 83, No. 11, Jun. 5, 1991.

Liver barrier test

The liver barrier test was carried out by the Institute of Clinical Pharmacology of the University of Berne (Prof. Dr. R. Preisig) on rat livers which were left in situ and perfunded. Two concentrates according to the invention were studied in parallel, containing 2% ERGO-STEROL-10-UNDECENOATE (ERGO-C 11:1) and 2% ERGOSTEROL-all trans-RETINATE respectively. The concentrates were diluted 1:10, 1:100 and 1:1'000 with distilled water and then injected with Ringer solution. During each test running for 20 minutes 15 probes were taken. The analytical work was performed with capillary zone electrophoresis (25 kV constant) on a P/ACE System 2000, Version 1.50 of Beckman Instruments.

Result:

The hepatic barrier is completely passed by the concentrates, also those least diluted, within 10 to 12 minutes.

What we claim is:

1. A spontaneously dispersible concentrate which forms an ultramicroemulsion when diluted with water or a glucose solution comprising:

0.001 to 15% by weight of one or a combination of steryl ester compounds selected from the group consisting of compounds of formulae (I) to (XII):

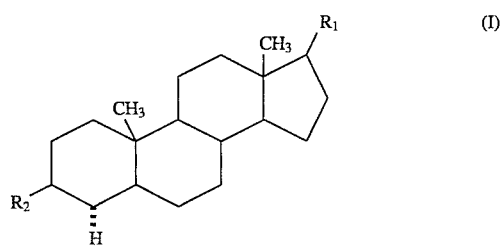

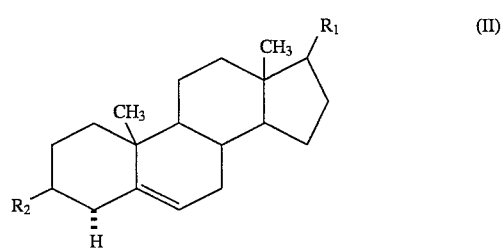

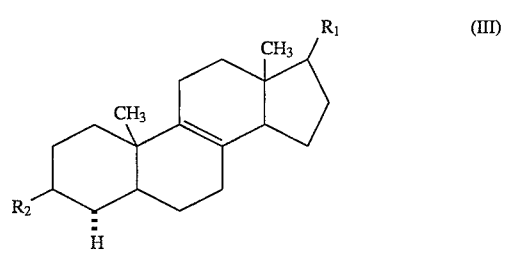

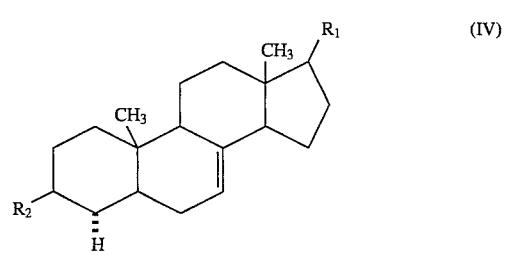

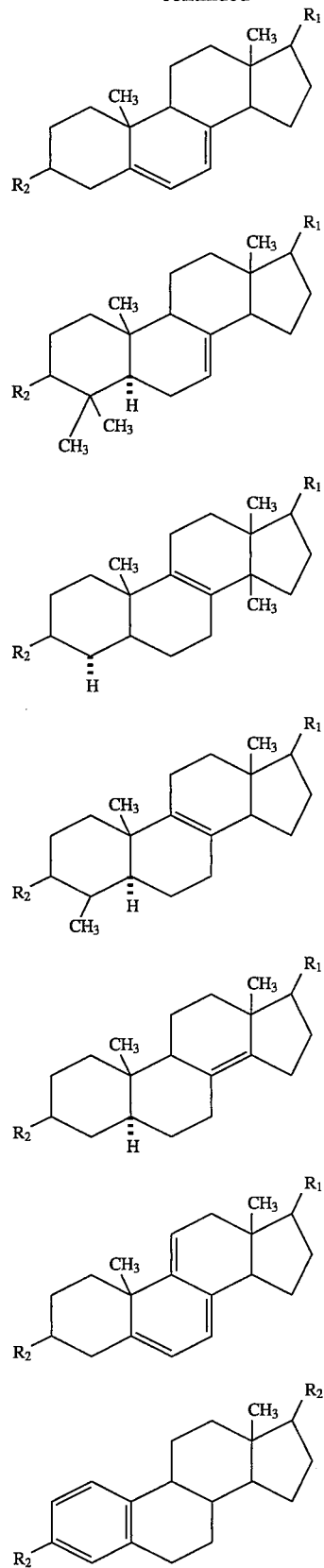

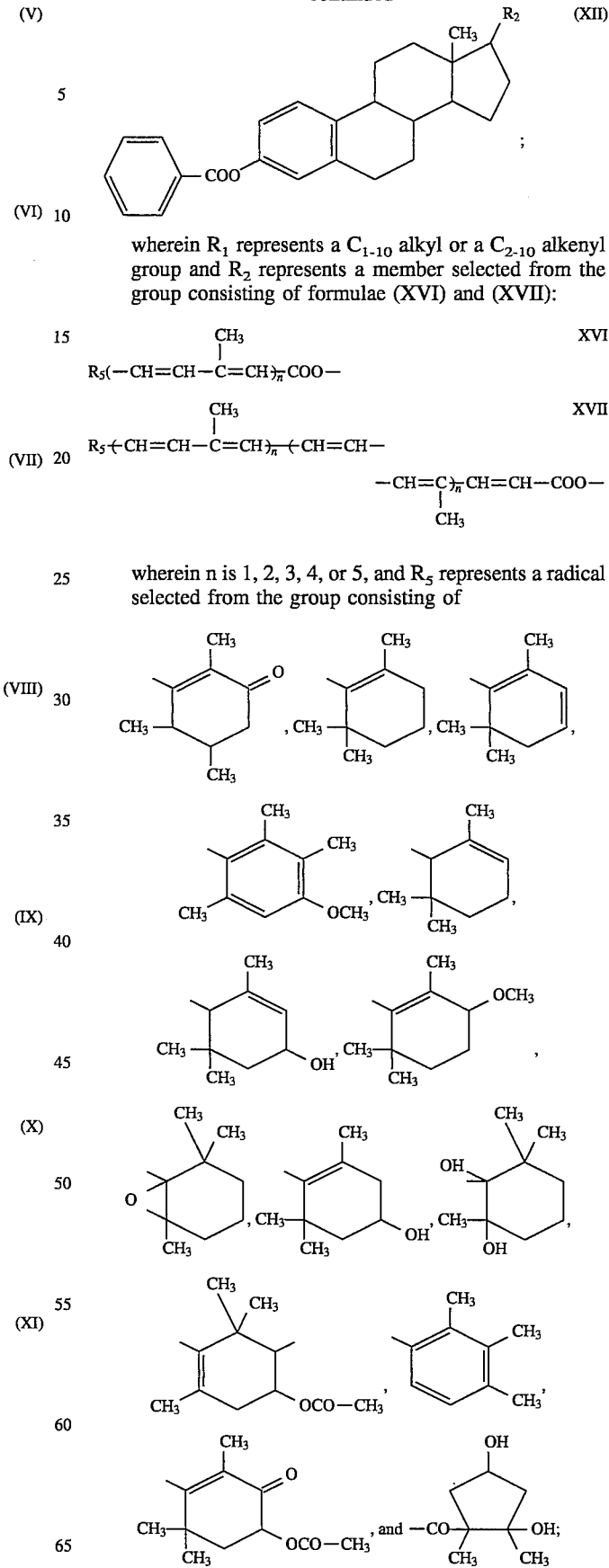

wherein $R_1$ represents a $C_{1-10}$ alkyl or a $C_{2-10}$ alkenyl group and $R_2$ represents a member selected from the group consisting of formulae (XVI) and (XVII):

$$R_5(-CH=CH-\underset{CH_3}{\underset{|}{C}}=CH)_n COO- \qquad XVI$$

$$R_5(CH=CH-\underset{CH_3}{\underset{|}{C}}=CH)_n(CH=CH- \qquad XVII$$
$$-CH=\underset{CH_3}{\underset{|}{C}})_n CH=CH-COO-$$

wherein n is 1, 2, 3, 4, or 5, and $R_5$ represents a radical selected from the group consisting of 0 to 40% by weight of a pharmaceutically acceptable solvent or solvent mixture which acts as a hydrotropic agent or co-emulsifier;

0.001 to 90% by weight of a pharmaceutically acceptable surfactant or surfactant mixture;

0 to 10% by weight of a vitamin or provitamin, up to 10% by weight of a free fatty acid, and a pharmaceutically acceptable carrier or diluent.

2. A spontaneously dispersible concentrate as claimed in claim 1, which comprises:

0.001 to 15% by weight of a steryl ester compound of formulae (I) to (XII) or a combination thereof, 1 to 40% by weight of isopropylmyristate, isopropylpalmitate, or a neutral oil, 10 to 90% by weight of a pharmaceutically acceptable surfactant or surfactant mixture, 0 to 10% by weight of a vitamin or provitamin, up to 10% by weight of a free fatty acid, and a pharmaceutically acceptable carrier or diluent.

3. A spontaneously dispersible concentrate as claimed in claim 2, which comprises:

10% by weight of a steryl ester compound of formulae (I) to (XII) or a combination thereof, 10% by weight of isopropylmyristate, 40% by weight of a tert-octylphenylpolyoxyethylene ether having 9 to 10 oxyethylene groups, and 40% by weight of tristyrylphenolpolyoxyethylene-18-mono/dimethyl phosphoric acid ester.

4. A spontaneously dispersible concentrate as claimed in claim 2, which comprises:

2% by weight of a steryl ester compound of formulae (I) to (XII) or a combination thereof, 12% by weight of isopropylmyristate, 43% by weight of a tert-octylphenylpolyoxyethylene ether having 9 to 10 oxyethylene groups, and 43% by weight of tristyrylphenolpolyoxyethylene-18-mono/dimethyl phosphoric acid ester.

5. A composition which inhibits the growth of tumor cells comprising 25 parts by weight of a spontaneously dispersible concentrate as claimed in claim 4, 44 parts by weight of a core material for granules or pellets, and 31 parts by weight of an enteric coating comprising hydroxypropyl methyl acetate succinate.

6. A spontaneously dispersible concentrate as claimed in claim 1, which comprises:

0.001 to 15% by weight of a steryl ester compound of formulae (I) to (XII) or a combination thereof, 1 to 40% by weight of isopropylmyristate, isopropylpalmitate, or a neutral oil, 20 to 45% by weight of a tert-octylphenylpolyoxyethylene ether having 9 to 10 oxyethylene groups, 20 to 45% by weight of (i) a surfactant mixture consisting of 50% by weight of each of the following two compounds:

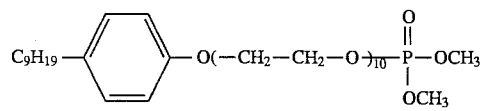

-continued

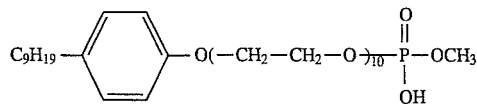

or of (ii) the following surfactant:

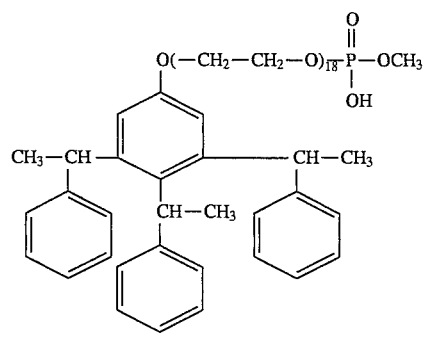

0 to 10% by weight of a vitamin or provitamin, up to 10% by weight of a free fatty acid, and a pharmaceutically acceptable carrier or diluent.

7. An composition which inhibits the growth of tumor cells comprising 1 to 95% by weight of a spontaneously dispersible concentrate as claimed in claim 1, wherein said composition is in the form of micropellets, granules, dragees, suppositories, ampules, or capsules.

8. A steryl ester selected from the group consisting of compounds of formulae (I) to (XII):

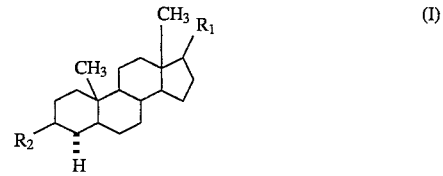

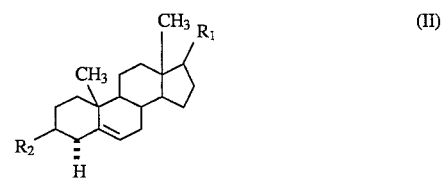

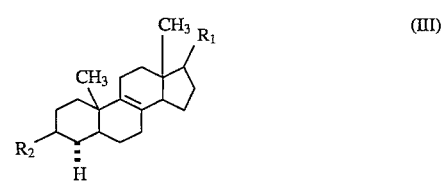

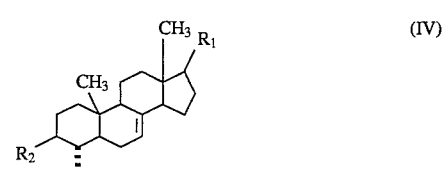

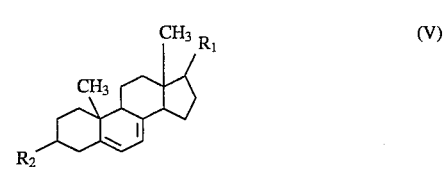

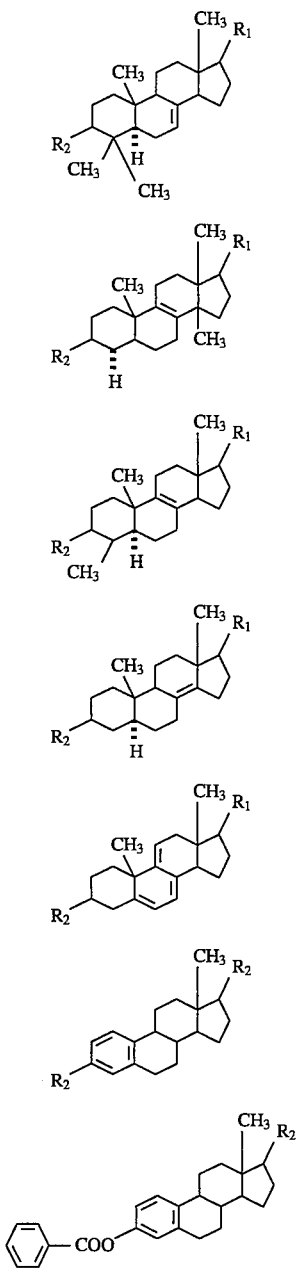
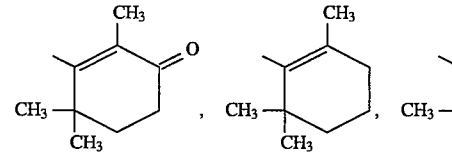
wherein R₁ represents a $C_{1-10}$ alkyl or a $C_{2-10}$ alkenyl group and R₂ represents a member selected from the group consisting of formulae (XVI) and (XVII):
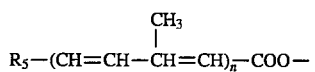
(XVI)
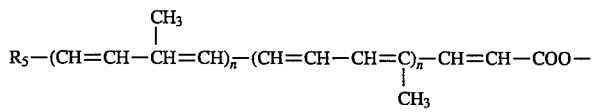
(XVII)
wherein n is 1, 2, 3, 4, or 5, and R₅ represents a radical selected from the group consisting of
or R₅ represents a group of formula (XX) or (XXII):

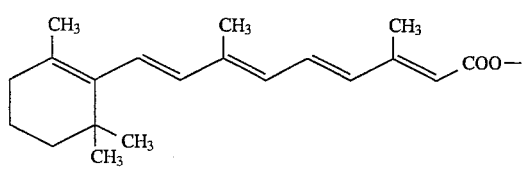 (XX)
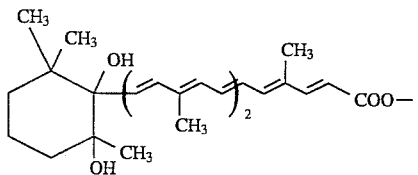 (XXII)
with the proviso that the ester is not cholest-5-en-3-all trans retinate.
9. A steryl ester as claimed in claim 8 selected from the group consisting of stigmasteryl-all trans retinate, stigmasteryl-13-cis-retinate, ergosteryl-all trans-retinate, and ergosteryl-13-cis-retinate.
* * * * *